United States Patent [19]

Crocker et al.

[11] Patent Number: 6,096,742

[45] Date of Patent: Aug. 1, 2000

[54] POLYMORPHIC FORM OF A TACHYKININ RECEPTOR ANTAGONIST

[75] Inventors: Louis Crocker; James McCauley, both of Belle Mead, N.J.

[73] Assignee: Merck & Co., Inc., Rahway, N.J.

[21] Appl. No.: 09/212,511

[22] Filed: Dec. 15, 1998

Related U.S. Application Data

[63] Continuation of application No. 09/108,567, Jul. 1, 1998, abandoned.

[60] Provisional application No. 60/051,600, Jul. 2, 1997.

[51] Int. Cl.⁷ ................................................. A61K 31/53
[52] U.S. Cl. ........................ 514/241; 544/132; 514/236.2
[58] Field of Search ........................... 544/132; 514/236.2

[56] References Cited

U.S. PATENT DOCUMENTS 5,719,147  2/1998  Dorn et al. .

FOREIGN PATENT DOCUMENTS

WO 94/00440  6/1993  WIPO .
WO 95/16679  12/1994  WIPO .

OTHER PUBLICATIONS

Crocker, L. S. et al., "Polymorphism of a Pharmaceutical Compound", Poster Presentation at 13th International Conf. on the Chem. of the Organic Solid State, Stony Brook, LI, NY, Jul. 13–18, 1997.

*Primary Examiner*—James H. Reamer
*Attorney, Agent, or Firm*—J. Eric Thies; David L. Rose

[57] ABSTRACT

This invention is concerned with a novel polymorphic form of the compound 2-(R)-(1-(R)-(3,5-bis(trifluoromethyl)-phenyl)-ethoxy)-3-(S)-(4-fluoro)phenyl-4-(3-(5-oxo-1H, 4H-1,2,4-triazolo)methylmorpholine which is a tachykinin receptor antagonist useful in the treatment or prevention of disorders of the central nervous system, inflammatory diseases, pain or migraine, asthma, and emesis. The instant polymorphic form has advantages over the other known forms of 2-(R)-(1-(R)-(3,5-bis(trifluoro-methyl)-phenyl) ethoxy)-3-(S)-(4-fluoro)phenyl-4-(3-(5-oxo-1H,4H-1,2,4-triazolo)methylmorpholine in terms of thermodynamic stability and suitability for inclusion in pharmaceutical formulations.

8 Claims, 2 Drawing Sheets

POLYMORPHIC FORM OF A TACHYKININ RECEPTOR ANTAGONIST

CROSS REFERENCE TO RELATED APPLICATIONS

This application is a continuation of application U.S. Ser. No. 09/108,567, filed Jul. 1, 1998, now abandoned which claims priority under 35 U.S.C. § 119(e) from U.S. Ser. No. 60/051,600, filed Jul. 2, 1997.

SUMMARY OF THE INVENTION

This invention is concerned with a novel polymorphic form of the compound: 2-(R)-(1-(R)-(3,5-bis (trifluoromethyl)-phenyl)ethoxy)-3-(S)-(4-fluoro)phenyl-4-(3-(5-oxo-1H,4H-1,2,4-triazolo)methylmorpholine.

The present invention is also concerned with pharmaceutical formulations comprising this novel polymorphic form of the compound as an active ingredient and the use of the compound and its formulations in the treatment of certain disorders.

The novel polymorphic form of this invention is a tachykinin receptor antagonist useful in the in the treatment or prevention of disorders of the central nervous system, inflammatory diseases, pain or migraine, asthma, and emesis.

This polymorphic form has advantages over the other known forms of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methyl-morpholine in terms of thermodynamic stability and suitability for inclusion in pharmaceutical formulations.

BACKGROUND OF THE INVENTION

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition. Substance P (also called "SP" herein) is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence Phe-X-Gly-Leu-Met-$NH_2$. In addition to SP the known mammalian tachykinins include neurokinin A and neurokinin B. The current nonmenclature designates the receptors for SP, neurokinin A, and neurokinin B as NK-1, NK-2, and NK-3, respectively.

Substance P is a pharmacologically-active neuropeptide that is produced in mammals and acts as a vasodilator, a depressant, stimulates salivation and produces increased capillary permeability. It is also capable of producing both analgesia and hyperalgesia in animals, depending on dose and pain responsiveness of the animal.

Evidence has been reviewed for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia.

It has furthermore been suggested that tachykinin receptor antagonists have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus, ophthalmic diseases such as conjunctivitis, vernal conjunctivitis, and the like, and cutaneous diseases such as contact dermatitis, atopic dermatitis, urticaria, and other eczematoid dermatitis.

Attempts have been made to provide antagonists for the receptors of substance P and other tachykinin peptides in order to more effectively treat the various disorders and diseases mentioned above. In particular, PCT Publication No. WO 94/00440, EPO Publication No. 0,577,394 and PCT Publication No. WO 95/16679 disclose certain morpholine and thiomorpholine compounds as substance P antagonists. In particular, the compound 2-(R)-(1-(R)-(3,5-bis (trifluoromethyl)-phenyl)ethoxy)-3-(S)-(4-fluoro)phenyl-4-(3-(5-oxo-1H,4H-1,2,4-triazolo)methylmorpholine is disclosed as the title compound of Example 75 of PCT Publication No. WO 95/16679.

Morphological forms of pharmaceutical compounds may be of interest to those involved in the development of a suitable dosage form because if the morphological form is not held constant during clinical and stability studies, the exact dosage used or measured may not be comparable from one lot to the next. Once a pharmaceutical compound is produces for use, it is important to recognize the morphological form delivered in each dosage form to assure that the production process use the same form and that the same amount of drug is included in each dosage. Therefore, it is imperative to assure that either a single morphological form or some known combination of morphological forms is present. In addition, certain morphological forms may exhibit enhanced thermodynamic stability and may be more suitable than other morphological forms for inclusion in pharmaceutical formulations. As used herein, a polymorphic form of a chemical compound is the same chemical entity, but in a different crystalline arrangement.

DETAILED DESCRIPTION OF THE INVENTION

Figure 1:
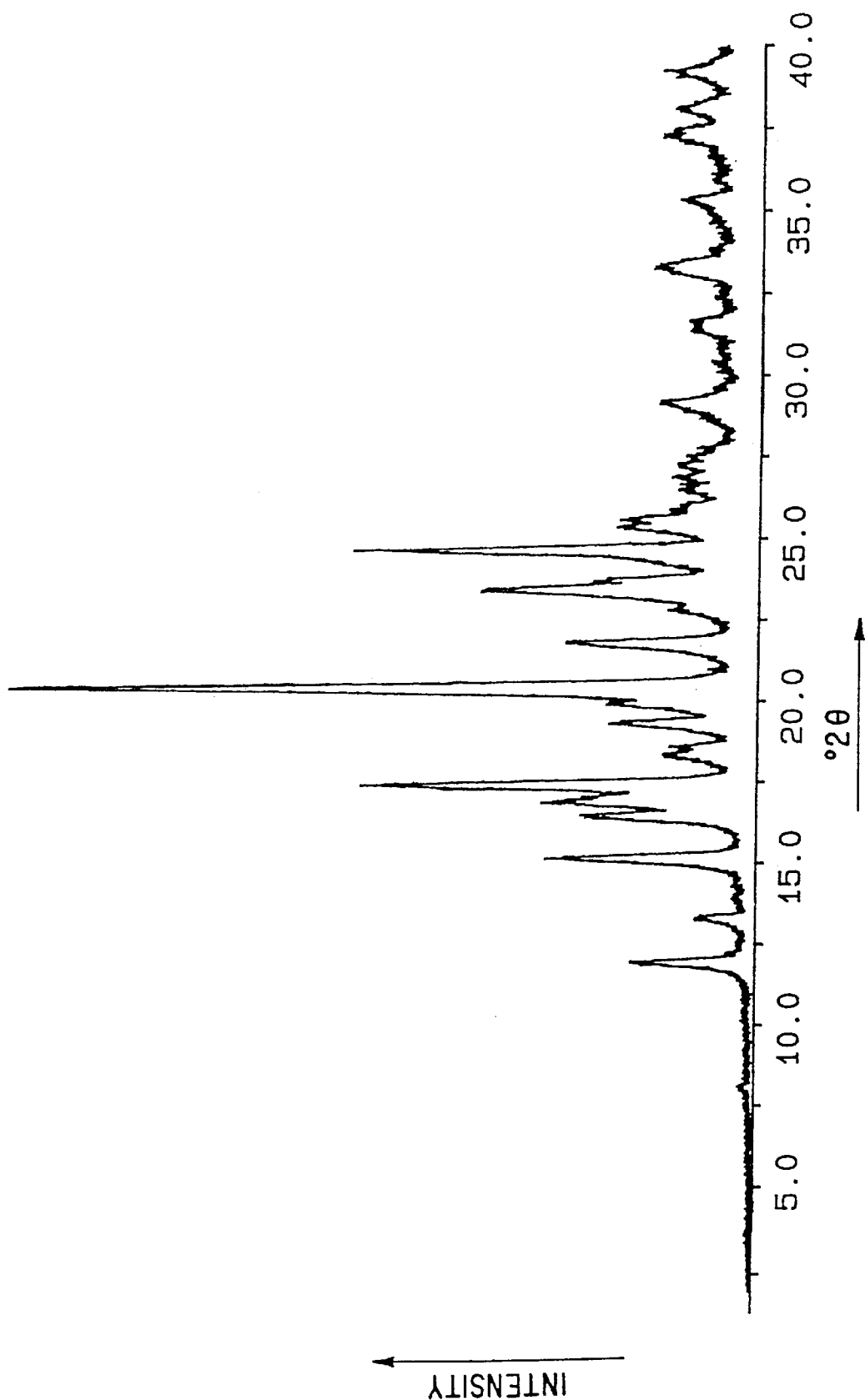
FIG. 1 is an X-ray powder diffraction pattern of Form I of 2-(R)-(1-(R)-(3,5-bis(trifluoromethyl)-phenyl)ethoxy)-3-(S)-(4-fluoro)-phenyl-4-(3-(5-oxo-1H,4H-1,2,4-triazolo) methylmorpholine.

The present invention is directed to a novel polymorphic form of the compound 2-(R)-(1-(R)-(3,5-bis (trifluoromethyl)-phenyl)ethoxy)-3-(S)-(4-fluoro)phenyl-4-(3-(5-oxo-1H,4H-1,2,4-triazolo)methylmorpholine and the process for the preparation of this polymorphic form.

The compound 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine has the structure:

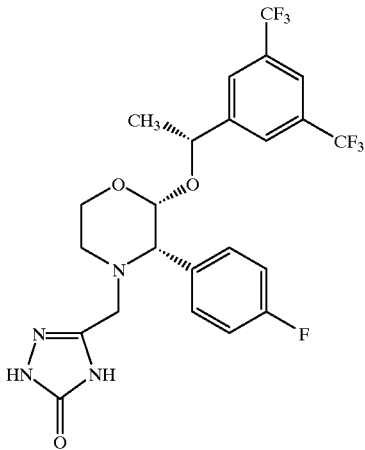

and is a tachykinin receptor antagonist useful in the treatment of inflammatory diseases, pain or migraine, asthma, and emesis.

This particular polymorphic form (herebin designated "Form I") has superior properties over other crystalline forms of the compound in that it is thermodynamically more stable than other morphological forms and is more suitable for inclusion in pharmaceutical formulations.

The present invention is also concerned with a process for the preparation of Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine which comprises:
    equilibrating Form II of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine in a solvent which is selected from: ethanol, 2-propanol, acetonitrile, and isopropyl acetate.

The present invention is further concerned with a process for the preparation of Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine which comprises:
    heating a sample of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine of optional morphological composition to a temperature range of 215 to 230° C.; and then
    returning the sample to ambient temperature.

In particular, the heating of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine may be conducted in a differential scanning calorimetric cell in an open pan under a nitrogen atmosphere and the 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine may be heated to a temperature of about 215–230° C., and then be cooled to room temperature. Preferably the morphological composition of the starting 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine is Form II.

In addition, the present invention is concerned with an alternative process particularly useful for the preparation of Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine on a larger scale comprising:
    suspending 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine of optional morphological composition in solution of methanol/water, which solution is preferably in a ratio of 2/1 (v/v);
    adding seed crystals of Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine;
    stirring the resultant mixture at about 0–50° C. for a period sufficient to result in the formation of Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine; and
    collecting the resultant Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine.

Similarly, the present invention is also directed to a process for the preparation of morphologically homogeneous 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine, comprising any of the aforementioned processes.

The compound of this invention, the novel polymorphic form of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine, is a tachykinin receptor antagonists useful in the treatment of inflammatory diseases, pain or migraine, asthma, and emesis. Accordingly, the present invention is further concerned with pharmaceutical formulations comprising this polymorphic form as an active ingredient, and the use of this polymorphic form and its formulations in the treatment of certain disorders.

Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine is anhydrous and non-hygroscopic and exhibits a high degree of thermal stability as a neat solid and in hydroalcoholic solution.

Form II is an anhydrous crystalline material melting at 254° C. which is obtained directly from recrystallization in the chemical synthesis of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methyl-morpholine.

X-Ray Powder Diffraction (XRPD)

Figure 2:
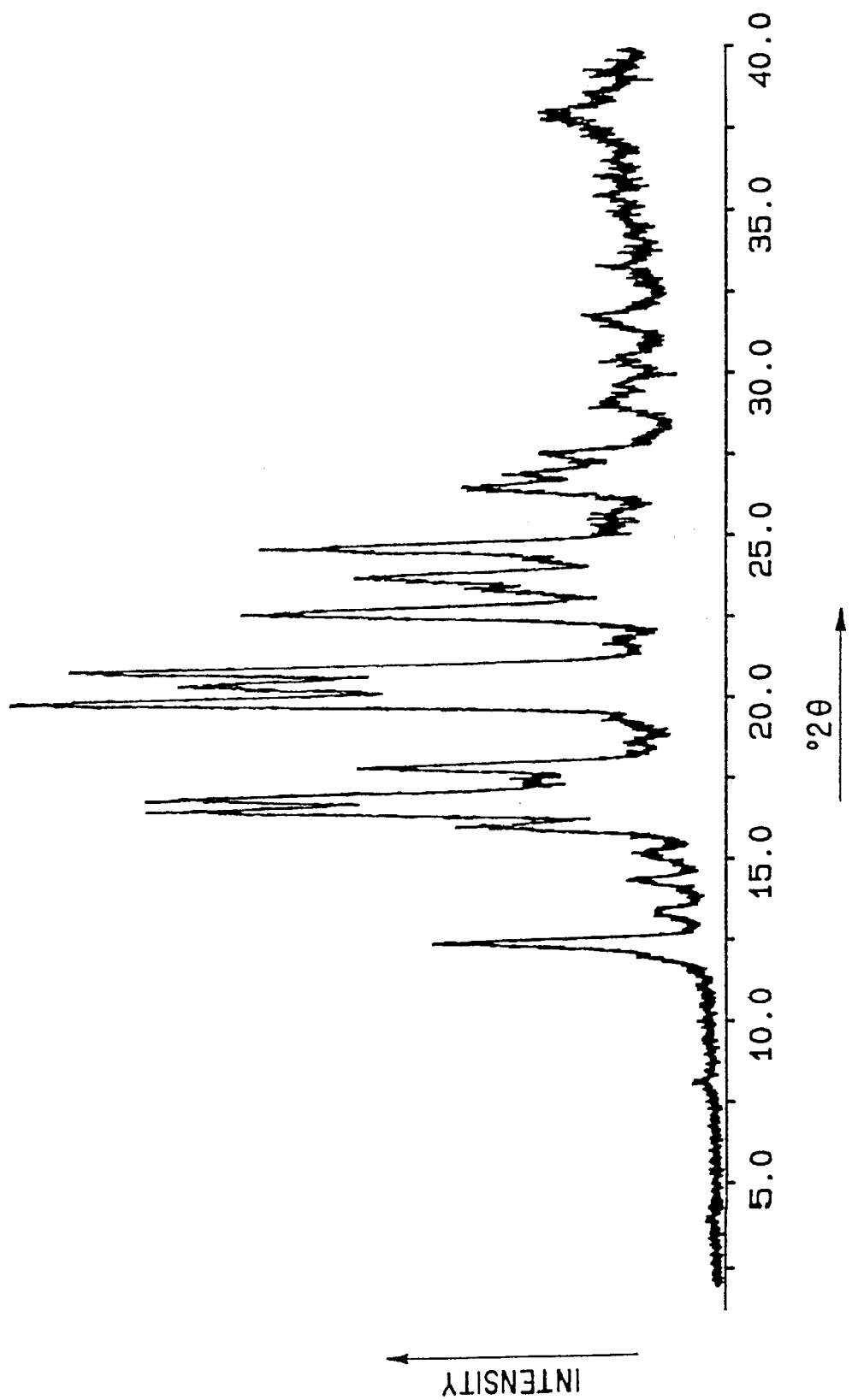
FIG. 2 is an X-ray powder diffraction pattern of Form II of 2-(R)-(1-(R)-(3,5-bis(trifluoromethyl)-phenyl)ethoxy)-3-(S)-(4-fluoro)-phenyl-4-(3-(5-oxo-1H,4H-1,2,4-triazolo) methylmorpholine.

X-Ray powder diffraction studies have been widely used to elucidate molecular structures, crystallinity and polymorphism. X-ray powder diffraction (XRPD) patterns were recorded using a Philips moded APD 3720 powder diffractometer equipped with a 3 kw X-ray generator (CuKα1 radiation) and a NaI (Ti) scintillation detector. Measurements were made from 3° to 45° (2 theta) with the sample maintained at ambient room temperature and are presented in FIG. 1 and FIG. 2.

Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine was characterized by an X-ray powder diffraction pattern with key reflections at approximately: 12.0, 15.3, 16.6, 17.0, 17.6, 19.4, 20.0, 21.9, 23.6, 23.8, and 24.8° (2 theta).

Form II of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine was characterized by an X-ray powder diffraction pattern with key reflections at approximately: 12.6, 16.7, 17.1, 17.2, 18.0, 20.1, 20.6, 21.1, 22.8, 23.9, and 24.8° (2 theta).

These XRPD patterns confirm that both samples are distinct crystalline forms. Both Form I and Form II exhibit intense peaks characteristic of crystalline material.

Differential Scanning Calorimeteric Cell [DSC]

Differential scanning calorimetry of Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo) methylmorpholine and of Form II of 2-(R)-(1-(R)-(3,5-bis (trifluoromethyl)-phenyl)ethoxy)-3-(S)-(4-fluoro)phenyl-4-(3-(5-oxo-1H,4H-1,2,4-triazolo)methylmorpholine showed no significant differences in their thermal behavior. Both phases produced thermograms with a single melting endotherm at the same temperature.

In particular, the DSC curve of Form I of 2-(R)-(1-(R)-(3,5-bis(trifluoromethyl)-phenyl)ethoxy)-3-(S)-(4-fluoro) phenyl-4-(3-(5-oxo-1H,4H-1,2,4-triazolo) methylmorpholine exhibited a single melting endotherm with a peak temperature of 255.8° C., an extrapolated onset temperature of 254.7° C., and an enthalpy of 105 J/g. The DSC curve of Form II of 2-(R)-(1-(R)-(3,5-bis (trifluoromethyl)-phenyl)ethoxy)-3-(S)-(4-fluoro)phenyl-4-(3-(5-oxo-1H,4H-1,2,4-triazolo)methylmorpholine also exhibited a single melting endotherm with a peak temperature of 255.6° C., an extrapolated onset temperature of 254.4° C., and an enthalpy of 107 J/g.

NMR

Proton and carbon nuclear magnetic resonance spectra on Form I and Form II indicated no chemical change in the compound in the conversion from Form II to Form I.

Solubility

The solubility of Form I in 2/1 (v/v) methanol/water at 0° C. was determined to be 0.9±0.1 mg/ml. The solubility of Form II in 2/1 (v/v) methanol/water at 0° C. was determined to be 1.3±0.2 mg/ml. The ratio of the solubilities is 1.4 which indicates that Form I is the more stable polymorph. Form I is more stable than Form II by 0.2 kcal/mol.

Vapor Pressures

The vapor pressures of Form I and Form II at elevated temperatures were similar when examined with Knudsen effusion techniques.

TACHYKININ ANTAGONISM ASSAY

The compound of this invention, the polymorphic Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo) methylmorpholine, is useful for antagonizing tachykinins, in particular substance P and neurokinin A in the treatment of gastrointestinal disorders, central nervous system disorders, inflammatory diseases, pain or migraine, asthma, and emesis in a mammal in need of such treatment. This activity may be demonstrated by the following assay.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-Sp, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1X8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter.

The activity of the present compound may also be demonstrated by the assay disclosed by Lei, et al., *British J. Pharmacol.*, 105, 261–262 (1992).

The compound of the present invention is of value in the treatment of a wide variety of clinical conditions which are characterized by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compound of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compound of the present invention is also of value in the treatment of a combination of the above conditions, in particular in the treatment of combined post-operative pain and post-operative nausea and vomiting.

The compound of the present invention is particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compound of the present invention is of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for example, by D. J. Stewart in "Nausea and Vomiting: Recent Research and Clinical Advances", Eds. J. Kucharczyk, et al., CRC Press Inc., Boca Raton, Fla., USA (1991), pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, and chlorambucil [R. J. Gralla, et al., *Cancer Treatment Reports*, 68(1), 163–172 (1984)].

The compound of the present invention is also of use in the treatment of emesis induced by radiation including radiation therapy such as in the treatment of cancer, or radiation sickness; and in the treatment of post-operative nausea and vomiting.

For the treatment of certain conditions it may be desirable to employ the compound of the present invention in conjunction with another pharmacologically active agent. It will be appreciated that the compound of the present invention may be presented together with another therapeutic agent as a combined preparation for simultaneous, separate or sequential use for the relief of emesis. Such combined preparations may be, for example, in the form of a twin pack.

A further aspect of the present invention comprises the compound of the present invention in combination with a 5-HT$_3$ antagonist, such as ondansetron, granisetron, tropisetron or zatisetron, or other anti-emetic medicaments, for example, dexamethasone or a dopamine antagonist such as metoclopramide. Additionally, the compound of the present invention may be administered in combination with an anti-inflammatory corticosteroid, such as dexamethasone. Furthermore, the compound of the present invention may be administered in combination with a chemotherapeutic agent such as an alkylating agent, antimetabolite, mitotic inhibitor or cytotoxic antibiotic, as described above. In general, the currently available dosage-forms of the known therapeutic agents for use in such combinations will be suitable.

When tested in the ferret model of cisplatin-induced emesis described by F. D. Tattersall et al, in *Eur. J. pharmacol.*, (1993) 250, R5–R6, the compound of the present invention was found to attenuate the retching and vomiting induced by cisplatin.

The compound of the present invention is also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain. The present invention further provides the compound of the present invention for use in therapy.

According to a further or alternative aspect, the present invention provides compound of the present invention for use in the manufacture of a medicament for the treatment or prevention of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of the compound of the present invention or a composition comprising the compound of the present invention.

For the treatment of certain conditions it may be desirable to employ a compound according to the present invention in conjunction with another pharmacologically active agent. For example, for the treatment of respiratory diseases such as asthma, the compound of the present invention may be used in conjunction with a bronchodilator, such as a $\beta_2$-adrenergic receptor antagonist or tachykinin antagonist which acts at NK-2 receptors. The compound of the present invention and the bronchodilator may be administered to a patient simultaneously, sequentially or in combination. For the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis, the compound of the present invention may be used in conjunction with a tachykinin antagonist which acts at neurokinin-2 receptors, or with tachykinin receptor antagonist which acts at both neurokinin-1 and neurokinin-2 receptors.

Likewise, the compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of the compound of the present invention and an effective amount of a bronchodilator. The present invention also provides a composition comprising the compound of the present invention, a bronchodilator, and a pharmaceutically acceptable carrier.

It will be appreciated that for the treatment or prevention of migraine, the compound of the present invention may be used in conjunction with other anti-migraine agents, such as ergotamines or 5-HT$_1$ agonists, especially sumatriptan or rizatriptan. Likewise, for the treatment of behavioural hyperalgesia, the compound of the present invention may be used in conjunction with an antagonist of N-methyl D-aspartate (NMDA), such as dizocilpine. For the treatment or prevention of inflammatory conditions in the lower urinary tract, especially cystitis, the compound of the present invention may be used in conjunction with an anti-inflammatory agent such as a bradykinin receptor antagonist. The present invention also provides a composition comprising the compound of the present invention, a bronchodilator, and a pharmaceutically acceptable carrier.

It will be appreciated that for the treatment or prevention of pain or nociception, the compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, afenantil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, afenantil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising the compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be further appreciated that for the treatment or prevention of depression and/or anxiety the compound of the present invention may be used in combination with an antidepressant agent or anti-anxiety agent. Suitable classes of antidepressant agents of use in the present invention include: norepinephrine reuptake inhibitors, selective serotonin include: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, α-adrenoreceptor antagonists and atypical antidepressants. Another class of antidepressant agent of use in the present invention are noradrenergic and specific serotonergic antidepressants, such as mirtazapine. Suitable examples of norepinephrine reuptake inhibitors include amitripdyline, clomipramine, doxepine, imipramine, trimipramine, amoxapine, desipramine, maprotiline, nortriptyline, reboxetine and protriptyline and pharmaceutically acceptable salts thereof. Suitable examples of selective serotonin reuptake inhibitors include fluoxetine, fluvoxamine, paroxetine, and sertraline and pharmaceutically acceptable salts thereof. Suitable examples of monoamine oxidase inhibitors include isocarboxazid, phenelzine, tranylcypromain and selegiline, and pharmaceutically acceptable salts thereof. Suitable examples of reversible monoamine oxidase inhibitors include moclobemide, and pharmaceutically acceptable salts thereof Suitable examples of serotonin and noradrenaline reuptake inhibitors include venlafaxine, and pharmaceutically acceptable salts thereof. Suitable examples of corticotropin releasing factor (CRF) antagonists include those compounds described in International Patent Specification Nos. WO 94/13643, WO 94/13644, WO 94/13661, WO 94/13676 and WO 94/13677. Suitable examples of atypical antidepressants include bupropion, lithium, nefazoedone, sibutramine, trazodone and viloxazine, and pharmaceutically acceptable salts thereof. Other antidepressants of use in the present invention include adinozolam, alaproclate, aminepine, amitryptyline/chlordiazepoxide combination, atipamezole, azamianserin, bazinaprine, fefuraline, bifemelane, binodaline, bipenamol, brofaromine, bupropion, caroxazone, cericlamine, cianopramine, cimoxatone, citalopram, clemeprol, clovoxamine, dasepinil, deanol, demexiptiline, dibenzepin, dothiepin, droxidopa, enefexine, setazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirindole, pizotyline, ritaserin, rolipram, sercloremine, setiptiline, sibutramine, sulbutiamine, sulpride, teniloxazine, thozalinone, thymoliberin, tianeptine, tiflucarbine, tofenacin, tofisopam, toloxatone, tomoxetine, veralipride, viqualine, zimelidine, and zometapine, and pharmaceutically acceptable salts thereof, and St. John's wort herb, or *Hypericum perforatum*, or extracts thereof. Preferred antidepressant agents include selective serotonin reuptake inhibitors, in particular, fluoxetine, fluvoxamine, paroxetine, and sertraline and pharmaceutically acceptable salts thereof Suitable classes of anti-anxiety agents of use in the present invention include benzodiazepines and 5-HT$_{1A}$ agonists or antagonists, especially 5-HT$_{1A}$ partial agonists, and corticotropin releasing factor (CRF) antagonists. In addition to benzodiazepines, other suitable classes of anti-anziety agents are nonbenzodiazepine sedative-hypnotic drugs such as zolpidem; mood-stabilizing drugs such as clobazam, gabapentin, lamotrigine, loreclezole, oxcarbamazepine, stiripentol and vigabatrin; and barbituates. Suitable banzodiazepines of use in the present invention include alprazolam, chlordizepoxide, clonazepam, chlorazepate, diazepam, halazepam, lorezepam, oxazepam and prazepam, and pharmaceutically acceptable salts thereof. Suitable examples of 5-HT$_{1A}$ agonists or antagonists of use in the present invention include, in particular, the 5-HT$_{1A}$ partial agonists buspirone, flesinoxan, gepirone, ipsapirone and pindolol, and pharmaceutically acceptable salts thereof. Suitable examples of corticotropin releasing factor (CRF) antagonists include those compounds described in International Patent Specification Nos. WO 94/13643, WO 94/13644, WO 94/13661, WO 94/13676 and WO 94/13677. Another class of anti-anxiety agent of use in the present invention are compounds having muscarinic cholinergic activity. Suitable compounds in this class include m 1 muscarinic cholinergic receptor antagonists such as those compounds described in European Patent Specification Nos. 0 709 093, 0 709 094 and 0 773 021 and International Patent Specification No. WO 96/12711. Another class of anti-anxiety agent of use in the present invention are compounds acting on ion channels. Suitable compounds in this class include carbamazepine, lamotrigine and valproate, and pharmaceutically acceptable salts thereof.

Therefore, in a further aspect of the present invention, there is provided a pharmaceutical composition comprising the compound of the present invention and an antidepressant or an anti-anxiety agent, together with at least one pharmaceutically acceptable carrier or excipient.

Suitable antipsychotic agents of use in combination with the compound of the present invention include the phenothiazine, thioxanthene, heterocyclic dibenzazepine, butyrophenone, diphenylbutylpiperidine and indolone classes of antipsychotic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. Suitable examples of dibenzazepines include clozapine and olanzapine. An example of a butyrophenone is haloperidol. An example of a diphenylbutylpiperidine is pimozide. An example of an indolone is molindolone. Other antipsychotic agents include loxapine, sulpiride and risperidone. It will be appreciated that the antipsychotic agents when used in combination with the compound of the present invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agnet of use in combination with the compound of the present invention include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with the compound of the present invention is the 5-HT$_{2A}$ receptor antagonists, examples of which include MDL100907 and fananserin. Also of use in combination with the compound of the present invention are the serotonin dopamine antagonists (SDAs) which are believed to combine 5-HT$_{2A}$ and dopamine receptor antagonist activity, examples of which include olanzapine and ziperasidone.

Therefore, in a further aspect of the present invention, there is provided a pharmaceutical composition comprising the compound of the present invention and an antipsychotic agent, together with at least one pharmaceutically acceptable carrier or excipient.

The compound of the present invention and the other pharmacologically active agent may be administered to a patient simultaneously, sequentially or in combination. It will be appreciated that when using a combination of the present invention, the compound of the present invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The pharmacological profile of the compound of the present invention offers the opportunity for their use in therapy at low doses thereby minimizing the risk of unwanted side effects.

The compound of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.01 to 5 mg/kg per day. A compound may be administered on a regimen of 1 to 4 times per day, preferably once or twice per day. In the treatment of emesis, a suitable dosage level is about 0.001 to 10 mg/kg per day, preferably about 0.005 to 5 mg/kg per day, and especially about 0.01 to 1 mg/kg per day. The compound may be administered on a regimen of 1 to 4 times per day, preferably once or twice per day. In the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compound may be administered on a regimen of 1 to 4 times per day, preferably once or twice per day.

It will be appreciated that the amount of the compound of the present invention required for use in any treatment will vary not only with the particular compounds or composition selected but also with the route of administration, the nature of the condition being treated, and the age and condition of the patient, and will ultimately be at the discretion of the attendant physician.

The pharmaceutical compositions of this invention may be used in the form of a pharmaceutical preparation, for example, in solid, semisolid or liquid form, which contains one or more of the compound of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Methods for preparing the polymorphic forms of this invention are illustrated in the following Examples. The following examples are given for the purpose of illustrating the present invention and shall not be construed as being limitations on the scope or spirit of the instant invention.

EXAMPLE 1

(S)-(4-Fluorophenyl)glycine Via Chiral Synthesis
Step A: 3-(4-Fluorophenyl)acetyl-4-(S)-benzyl-2-oxazolidinone An oven-dried, 1 L 3-necked flask, equipped with a septum, nitrogen inlet, thermometer, and a magnetic stirring bar, was flushed with nitrogen and charged with a solution of 5.09 g (33.0 mmol) of 4-fluorophenylacetic acid in 100 mL of anhydrous ether. The solution was cooled to −10° C. and treated with 5.60 mL (40.0 mmol) of triethylamine followed by 4.30 mL (35.0 mmol) of trimethylacetyl chloride. A white precipitate formed immediately. The resulting mixture was stirred at −10° C. for 40 minutes, then cooled to −78° C.

An oven-dried, 250 mL round bottom flask, equipped with a septum and a magnetic stirring bar, was flushed with nitrogen and charged with a solution of 5.31 g (30.0 mmol) of 4-(S)-benzyl-2-oxazolidinone in 40 mL of dry THF. The solution was stirred in a dry ice/acetone bath for 10 minutes, then 18.8 mL of 1.6 M n-butyllithium solution in hexanes was slowly added. After 10 minutes, the lithiated oxazolidinone solution was added, via cannula, to the mixture in the 3-necked flask. The cooling bath was removed from the resulting mixture and the temperature was allowed to rise to 0° C. The reaction was quenched with 100 mL of saturated aqueous ammonium chloride solution, transferred to a 1 L flask, and the ether and THF were removed in vacuo. The concentrated mixture was partitioned between 300 mL of methylene chloride and 50 mL of water and the layers were separated. The organic layer was washed with 200 mL of 2 N aqueous hydrochloric acid solution, 300 mL of saturated aqueous sodium bicarbonate solution, dried over magnesium sulfate and concentrated in vacuo. Flash chromatography on 400 g of silica gel using 3:2 v/v hexanes/ether as the eluant afforded 8.95 g of an oil that slowly solidified on standing. Recrystallization from 10:1 hexanes/ether afforded 7.89 g (83%) of the title compound as a white solid, mp 64–66° C. Mass Spectrum (FAB): m/Z 314 (M+H, 100%), 177 (M−ArCH$_2$CO+H, 85%). $^1$H-NMR (400 MHz, CDCl$_3$): δ 2.76 (dd, 1 H, J=13.2, 9.2), 3.26 (dd, J=13.2, 3.2), 4.16–4.34 (m, 4 H), 4.65–4.70 (m, 1 H), 7.02–7.33 (m, 9 H). Analysis: Calcd for C$_{18}$H$_{16}$FNO$_3$: C,69.00; H, 5.15; N, 4.47; F, 6.06; Found: C, 68.86; H, 5.14; N, 4.48; F, 6.08.

Step B: 3-((S)-Azido-(4-fluorophenyl))acetyl-4-(S)-benzyl-2-oxazolidinone

An oven-dried, 1 L 3-necked flask, equipped with a septum, nitrogen inlet, thermometer, and a magnetic stirring bar, was flushed with nitrogen and charged with a solution of 58.0 mL of 1 M potassium bis(trimethylsilyl)amide solution in toluene and 85 mL of THF and was cooled to −78° C. An oven-dried, 250 mL round-bottomed flask, equipped with a septum and a magnetic stirring bar, was flushed with nitrogen and charged with a solution of 7.20 g (23.0 mmol) of 3-(4-fluorophenyl)acetyl-4-(S)-benzyl-2-oxazolidinone in 40 mL of THF. The acyl oxazolidinone solution was stirred in a dry ice/acetone bath for 10 minutes, then transferred, via cannula, to the potassium bis(trimethylsilyl)amide solution at such a rate that the internal temperature of the mixture was maintained below −70° C. The acyl oxazolidinone flask was rinsed with 15 mL of THF and the rinse was added, via cannula, to the reaction mixture and the resulting mixture was stirred at −78° C. for 30 minutes. An oven-dried, 250 mL round-bottomed flask, equipped with a septum and a magnetic stirring bar, was flushed with nitrogen and charged with a solution of 10.89 g (35.0 mmol) of 2,4,6-triisopropylphenylsulfonyl azide in 40 mL of THF. The azide solution was stirred in a dry ice/acetone bath for 10 minutes, then transferred, via cannula, to the reaction mixture at such a rate that the internal temperature of the mixture was maintained below −70° C. After 2 minutes, the reaction was quenched with 6.0 mL of glacial acetic acid, the cooling bath was removed and the mixture was stirred at room temperature for 18 hours. The quenched reaction mixture was partitioned between 300 mL of ethyl acetate and 300 mL of 50% saturated aqueous sodium bicarbonate solution. The organic layer was separated, dried over magnesium sulfate, and concentrated in vacuo. Flash chromatography on 500 g of silica gel using 2:1 v/v, then 1:1 v/v hexanesomethylene chloride as the eluant afforded 5.45 g (67%) of the title compound as an oil. IR Spectrum (neat, cm$^{-1}$): 2104, 1781, 1702. $^1$H-NMR (400

MHz, CDCl$_3$): δ 2.86 (dd, 1 H, J=13.2, 9.6), 3.40 (dd, 1 H, J=13.2, 3.2), 4.09–4.19 (m, 2 H), 4.62–4.68 (m, 1 H), 6.14 (s, 1 H), 7.07–7.47 (m, 9 H). Analysis: Calcd for C$_{18}$H$_{15}$FN$_4$O$_3$: C, 61.01; H, 4.27; N, 15.81; F, 5.36; Found: C, 60.99; H, 4.19; N, 15.80; F, 5.34.

Step C: (Sr)-Azido-(4-fluorophenyl)acetic acid

A solution of 5.40 g (15.2 mmol) of 3-((S)-azido-(4-fluorophenyl))acetyl-4-(S)-benzyl-2-oxazolidinone in 200 mL of 3:1 v/v THF/water was stirred in an ice bath for 10 minutes. 1.28 g (30.4 mmol) of lithium hydroxide monohydrate was added in one portion and the resulting mixture was stirred cold for 30 minutes. The reaction mixture was partitioned between 100 mL of methylene chloride and 100 mL of 25% saturated aqueous sodium bicarbonate solution and the layers were separated. The aqueous layer was washed with 2×100 mL of methylene chloride and acidified to pH 2 with 2 N aqueous hydrochloric acid solution. The resulting mixture was extracted with 2×100 mL of ethyl acetate; the extracts were combined, washed with 50 mL of saturated aqueous sodium chloride solution, dried over magnesium sulfate, and concentrated in vacuo to afford 2.30 g (77%) of the title compound as an oil that was used in the following step without further purification. IR Spectrum (neat, cm–1): 2111, 1724. $^1$H-NMR (400 MHz, CDCl$_3$): δ 5.06 (s, 1 H), 7.08–7.45 (m, 4 H), 8.75 (br s,1H).

Step D: (S)-(4-Fluorophenyl)glycine

A mixture of 2.30 g (11.8 mmol) of (S)-azido-(4-fluorophenyl)acetic acid, 250 mg 10% palladium on carbon catalyst and 160 mL 3:1 v/v water/acetic acid was stirred under an atmosphere of hydrogen for 18 hours. The reaction mixture was filtered through Clite and the flask and filter cake were rinsed well with ~1 L of 3:1 v/v water/acetic acid. The filtrate was concentrated in vacuo to about 50 mL of volume. 300 mL of toluene was added and the mixture concentrated to afford a solid. The solid was suspended in 1:1 v/v methanol/ether, filtered and dried to afford 1.99 g (100%) of the title compound. $^1$H-NMR (400 MHz, D$_2$O+NaOD): δ 3.97 (s, 1 H), 6.77 (app t, 2 H, J=8.8), 7.01 (app t, 2 H, J=5.6).

Via Resolution

Step A': 4-Fluorophenylacetyl chloride

A solution of 150 g (0.974 mol) of 4-fluorophenylacetic acid an 1 mL of N,N-dimethylformamide in 500 mL of toluene at 40° C. was treated with 20 mL of thionyl chloride and heated to 40° C. An additional 61.2 mL of thionyl chloride was added dropwise over 1.5 hours. After the addition, the solution was heated at 50° C. for 1 hour, the solvent was removed in vacuo and the residual oil was distilled at reduced pressure (1.5 mmHg) to afford 150.4 g (89.5%) of the title compound, bp=68–70° C.

Step B': Methyl 2-bromo-2-(4-fluoro)phenylacetate

A mixture of 150.4 g (0.872 mol) of 4-fluorophenylacetyl chloride and 174.5 g (1.09 mol) of bromine was irradiated at 40–50 ° C. with a quartz lamp for 5 hours. The reaction mixture was added dropwise to 400 mL of methanol and the solution was stirred for 16 hours. The solvent was removed in vacuo and the residual oil was distilled at reduced pressure (1.5 mmHg) to afford 198.5 g (92%) of the title compound, bp=106–110° C.

Step C': Methyl (±)-(4-fluorophenyl)glycinate

A solution of 24.7 g (0.1 mol) of methyl 2-bromo-2-(4-fluoro) phenylacetate and 2.28 g (0.01 mol) of benzyl triethylammonium chloride in 25 mL of methanol was treated with 6.8 g (0.105 mol) of sodium azide and the resulting mixture was stirred 20 hours at room temperature. The reaction mixture was filtered; the filtrate was diluted with 50 mL of methanol and hydrogenated in the presence of 0.5 g of 10% Pd/C at 50 psi for 1 hour. The solution was filtered and the solvent removed in vacuo. The residue was partitioned between 10% aqueous sodium carbonate solution and ethyl acetate. The organic phase was washed with water, saturated aqueous sodium chloride solution, dried over magnesium sulfate and concentrated in vacuo to afford 9.8 g of the title compound as an oil.

Step D': Methyl (S)-(4-fluorophenyl)glycinate

A solution of 58.4 g of methyl (±)-4-fluorophenylglycinate in 110 mL of 7:1 v/v ethanol/water was mixed with a solution of 28.6 g (0.0799 mol) of O,O'-(+)-dibenzoyltartaric acid ((+)-DBT) (28.6 g, 0.0799 mol) in 110 mL of 7:1 v/v ethanol: water and the resulting solution was allowed to age at room temperature. Ethyl acetate (220 ml) was added after crystallization was complete and the resulting mixture was cooled to –20° C. and filtered to afford 32.4 g of methyl (S)-(4-fluorophenyl) glycinate, (+)-DBT salt (ee=93.2%). The mother liquors were concentrated in vacuo and the free base was liberated by partitioning between ethyl acetate and aqueous sodium carbonate solution. A solution of free base, so obtained, in 110 mL of 7:1 v/v ethanol/water was mixed with a solution of 28.6 g (0.0799 mol) of O,O'-(–)-dibenzoyltartaric acid ((–)-DBT) (28.6 g, 0.0799 mol) in 110 mL of 7:1 v/v ethanol: water and the resulting solution was allowed to age at room temperature. Ethyl acetate (220 ml) was added after crystallization was complete and the resulting mixture was cooled to –20° C. and filtered to afford 47.0 g of methyl (R)-(4-fluorophenyl)glycinate, (–)-DBT salt (ee=75.8%). Recycling of the mother liquors and addition of (+)-DBT gave a second crop of 7.4 g of (S)-(4-fluorophenyl)glycinate, (+)-DBT salt (ee=96.4%). The two crops of the (S)-amino ester (39.8 g) were combined in 200 mL of 7:1 v/v ethanol/water, heated for 30 minutes and cooled to room temperature. Addition of ethyl acetate, cooling, and filtration afforded 31.7 g of (S)-(4-fluorophenyl)glycinate, (+)-DBT salt (ee>98%). Enatiomeric excesses was determined by chiral HPLC (Crownpak CR(+) 5% MeOH in aqHClO$_4$ pH2 1.5 ml/min 40° C. 200 nm). A mixture of 17.5 g of (S)-(4-fluorophenyl)glycinate, (+)-DBT salt and 32 mL of 5.5 N HCl (32 ml) was heated at reflux for 1.5 hours. The reaction mixture was concentrated in vacuo and the residue was dissolved in 40 mL of water. The aqueous solution was washed 3×30 mL of ethyl acetate and the layers were separated. The pH of the aqueous layer was adjusted to 7 using ammonium hydroxide and the precipitated solid was filtered to afford 7.4 g of the title compound (ee=98.8%).

EXAMPLE 2

3-(S)-(4-Fluorophenyl)-4-benzyl-2-morpholinone

Step A: N-Benzyl (S)-(4-fluorophenyl)glycine

A solution of 1.87 g (11.05 mmol) of (S)-(4-fluorophenyl)-glycine and 1.12 mL (11.1 mmol) of benzaldehyde in 11.1 mL of 1 N aqueous sodium hydroxide solution and 11 mL of methanol at 0° C. was treated with 165 mg (4.4 mmol) of sodium borohydride. The cooling bath was removed and the resulting mixture was stirred at room temperature for 30 minutes. Second portions of benzaldehyde (1.12 mL (11.1 mmol)) and sodium borohydride 165 mg (4.4 mmol) were added to the reaction mixture and stirring was continued for 1.5 hours. The reaction mixture was partitioned between 100 mL of ether and 50 mL of water and the layers were separated. The aqueous layer was separated and filtered to remove a small amount of insoluble material. The filtrate was acidified to pH 5 with 2 N aqueous hydrochloric acid solution and the solid that had precipitated was filtered, rinsed well with water, then ether, and dried to afford 1.95 g of the title compound. $^1$H-NMR (400 MHz, D$_2$0+NaOD): δ 3.33 (AB q, 2 H, J=8.4), 3.85 (s, 1 H), 6.79–7.16 (m, 4 H).

Step B: 3-(S)-(4-Fluorophenyl)-4-benzyl-2-morpholinone

A mixture of 1.95 g (7.5 mmol) of N-benzyl (S)-(4-fluorophenyl)glycine, 3.90 mL (22.5 mmol) of N,N-diisopropylethylamine, 6.50 mL (75.0 mmol) of 1,2-dibromoethane and 40 mL of N,N-dimethylformamide was stirred at 100° C. for 20 hours (dissolution of all solids occurred on warming). The reaction mixture was cooled and concentrated in vacuo. The residue was partitioned between 250 mL of ether and 100 mL of 0.5 N potassium hydrogen sulfate solution and the layers were separated. The organic layer was washed with 100 mL of saturated aqueous sodium bicarbonate solution, 3×150 mL of water, dried over magnesium sulfate, and concentrated in vacuo. Flash chromatography on 125 g of silica gel using 3:1 v/v hexanes/ether as the eluant afforded 1.58 g (74%) of the title compound as an oil. $^1$H-NMR (400 MHz, CDCl$_3$): δ 2.65 (dt, 1 H, J=3.2, 12.8), 3.00 (dt, 1 H, J=12.8, 2.8), 3.16 (d, 1 H, J=13.6), 3.76 (d, 1 H, J=13.6), 4.24 (s, 1 H), 4.37 (dt, 1 H, J=13.2,3.2), 4.54 (dt, 1 H,J=2.8,13.2), 7.07–7.56 (m,9 H).

EXAMPLE 3

2-(R)-(3,5-Bis(trifluoromethyl)benzoyloxy)-3-(S)-(4-fluoro)phenyl-4-benzyl morpholine A solution of 2.67 g (10.0 mmol) of 3-(R)-(4-fluoro)-phenyl-4-benzyl-2-morpholinone in 40 mL of dry THF was cooled to −78° C. The cold solution was treated with 12.5 mL of 1.0 M L-Selectride®, solution in THF, maintaining the internal reaction temperature below −70° C. The resulting solution was stirred cold for 45 minutes and the reaction was charged with 3.60 mL (20.0 mmol) of 3,5-bis(trifluoromethyl)benzoyl chloride. The resulting yellow mixture was stirred cold for 30 minutes and the reaction was quenched with 50 mL of saturated aqueous sodium bicarbonate solution. The quenched mixture was partitioned between 300 mL of ether and 50 mL of water and the layers were separated. The organic layer was dried over magnesium sulfate. The aqueous layer was extracted with 300 mL of ether; the extract was dried and combined with the original organic layer. The combined organics were concentrated in vacuo. Flash chromatography on 150 g of silica gel using 37:3 v/v hexanes/ether as the eluant afforded the title compound as a solid (83% yield).

Mass Spectrum (FAB): m/Z 528 (M+H, 25%), 270 (100%). $^1$H NMR (CDCl$_3$, 400 MHz, ppm): δ 2.50 (dt, J=3.2, 12.0, 1H), 2.96 (app d, J=12.0, 1H), 2.98 (d, J=13.6, 1H), 3.74–3.78 (m, 1H), 3.81 (d, J=2.8, 1H), 3.94 (d, J=13.6, 1H), 4.19 (dt, J=2.0, 12.0), 6.20 (d, J=2.8, 1H), 6.99 (t, J=8.4, 2H), 7.27–7.38 (m, 5H), 7.52–7.56 (m, 2H), 8.09 (s, 1H), 8.46 (s, 2H).

EXAMPLE 4

Dimethyl titanocene

A solution of 2.49 g (10.0 mmol) of titanocene dichloride in 50 mL of ether in the dark at 0° C. was treated with 17.5 mL of 1.4 M methyllithium solution in ether maintaining the internal temperature below 5° C. The resulting yellow/orange mixture was stirred at room temperature for 30 minutes and the reaction was quenched by slowly adding 25 g of ice. The quenched reaction mixture was diluted with 50 mL of ether and 25 mL of water and the layers were separated. The organic layer was dried over magnesium sulfate and concentrated in vacuo to afford 2.03 g (98%) of the title compound as a light-sensitive solid. The dimethyl titanocene could be stored as a solution in toluene at 0° C. for at least 2 weeks without apparent chemical degradation. $^1$H NMR (CDCl$_3$, 200 MHz, ppm): δ −0.15 (s, 6H), 6.06 (s, 10H).

EXAMPLE 5

2-(R)-(1-(3,5-Bis(trifluoromethyl)phenyl) ethenyloxy)-3-(S)-(4-fluoro)-phenyl-4-benzyl morpholine A solution of 4.9 mmol of 2-(R)-(3,5-bis (trifluoromethyl)-benzoyloxy)-3-(S)-(4-fluoro)phenyl-4-benzyl morpholine and 2.50 g (12.0 mmol) of dimethyl titanocene in 35 mL of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded of the title compound as a solid (60% yield).

Mass Spectrum (FAB): m/Z 526 (M+H, 75%), 270 (100%). $^1$H NMR (CDCl$_3$, 400 MHz, ppm): δ 2.42 (dt, J=3.6, 12.0), 2.90 (app d, J=12.0, 1H), 2.91 (d, J=13.6, 1H), 3.62–3.66 (m, 1H), 3.72 (d, J=2.6), 3.94 (d, J=13.6, 1H), 4.09 (dt, J=2.4, 12.0, 1H), 4.75 (d, J=3.2, 1H), 4.82 (d, J=3.2, 1H), 5.32 (d, J=2.6, 1H), 7.09 (t, J=8.8, 2H), 7.24–7.33 (m, 5H), 7.58–7.62 (m, 2H), 7.80 (s, 1H), 7.90 (s, 2H).

EXAMPLE 6

2-(R)-1-(S)-(3,5-Bis(trifluoromethyl)phenyl) ethoxy)-3-(S)-(4-fluoro)phenyl morpholine and 2-(S)-(1-(R)-(3,5-Bis(trifluoromethyl)-phenyl)ethoxy)-3-(S)-(4-fluoro)phenyl morpholine A mixture of 1.83 g (3.5 mmol) of 2-(R)-(1-(3,5-bis(trifluoromethyl)phenyl)ethenyloxy)-3-(S)-(4-fluoro)phenyl-4-benzyl morpholine and 800 mg 5% rhodium on alumina catalyst in 40 mL of absolute ethanol was stirred under an atmosphere of hydrogen for 24 hours. The catalyst was filtered onto a pad of Celite; the reaction flask and filter cake were rinsed with 200 mL of ethyl acetate. The filtrate was concentrated in vacuo and the residue was pumped under high vacuum (1 mmHg, room temperature) to dryness.

The residue was redissolved in 40 mL of isopropanol; 800 mg of 10% palladium on carbon catalyst was added and the resulting mixture was stirred under an atmosphere of hydrogen for 24 hours. The catalyst was filtered onto a pad of Celite; the reaction flask and filter cake were rinsed with 200 mL of ethyl acetate. The filtrate was concentrated in vacuo. Flash chromatography on 50 g of silica gel using 2:1 v/v hexanes/ether, then 3:2 v/v ether/hexanes as the eluant afforded 283 mg of $^2$-(R)-(1-(S)-(3,5-bis(trifluoromethyl) phenyl)-ethoxy)-3-(S)-(4-fluoro)phenyl morpholine and 763 mg of 2-(R)-(1-(R)-(3,5-bis(trifluoro-methyl)phenyl) ethoxy)-3-(S)-(4-fluoro)phenyl morpholine, both as oils (total yield 68%). For 2-(R)-(1-(S)-(3,5-bis(trifluoromethyl) phenyl)ethoxy)-3-(S)-(4-fluoro)phenyl morpholine: Mass Spectrum (FAB) m/Z 438 (M+H, 65%), 180 (100%). $^1$H NMR (CDCl$_3$, 400 MHz, ppm): δ 1.47 (d, J=6.8, 3H), 1.87 (br s, 1H), 3.03 (dd, J=2.8, 12.8), 3.17 (dt, J=4.0, 12.4, 1H), 3.43–3.47 (m, 1H), 3.80 (dt, J=3.2, 11.6), 4.10 (d, J=2.2, 1H), 4.70 (q, J=6.8, 1H), 4.87 (d, J=2.2, 1H), 6.99–7.03 (m, 2H), 7.23–7.27 (m, 2H), 7.63 (s, 2H), 7.66 (s, 1H). For 2-(R)-(1-(R)-(3,5-bis(trifluoromethyl)phenyl)ethoxy)-3-(S)-(4-fluoro)phenyl morpholine: Mass Spectrum (FAB)

m/Z 438 (M+H, 75%), 180 (100%). $^1$H NMR (CDCl$_3$, 400 MHz, ppm): δ 1.16 (d, J=6.8), 1.80 (br s, 1H), 3.13 (dd, J=3.2, 12.4), 3.23 (dt, J=3.6, 12.4), 3.63 (dd, J=2.4, 11.2), 4.01 (d, J=2.4, 1H), 4.13 (dt, J=3.2, 12.0), 4.42 (d, J=2.4, 1H), 4.19 (q, J=6.8, 1H), 7.04–7.09 (m, 2H), 7.27–7.40 (m, 4H), 7.73 (s, 1H).

EXAMPLE 7

2-(R)-(1-(R)-(3,5-Bis(trifluoromethyl)phenyl) ethoxy)-3-(S)-(4-fluoro)-phenyl-4-(3-(5-oxo-1,2,4-triazolo)methylmorpholine Step A: N-Methylcarboxy-2-chloroacetamidrazone A solution of 5.0 g (66.2 mmol) of chloroacetonitrile in 35 mL of dry methanol was cooled to 0° C. and was treated with 0.105 g (1.9 mmol) of sodium methoxide. The ice-bath was removed and the mixture was alowed to stir at room temperature for 30 minutes. To the reaction was then added 0.110 mL (1.9 mmol) of acetic acid and then 5.8 g (64.9 mmol) of methyl hydrazinecarboxylate. After stirring 30 minutes at room temperature, the suspension was concentrated in vacuo, and placed on the high-vac line overnight, to give 10.5 g (98%) of a yellow powder, a portion of which was employed in Step C below.

Step B: 2-(R)-(1-(R)-(3,5-Bis(trifluoromethyl)phenyl) ethoxy)-3-(S)-(4-fluoro)phenyl-4-(2-(N-methylcatboxy-acetamidrazono) morpholine A solution of 945 mg (2.3 mmol) of (2-(R)-(1-(R)-(3,5-bis(trifluoromethyl)phenyl)ethoxy)-3-(S)-(4-fluoro)phenyl morpholine, 447 mg (2.7 mmol) of N-methylcarboxy-2-chloro-acetamidrazone, and 0.78 mL (4.5 mmol) of N,N-diisopropylethylamine in 17 mL of acetonitrile was stirred at room temperature for 20 hours. The reaction was concentrated in vacuo and the residue was partitioned between 50 mL of methylene chloride and 25 mL of water. The organic layer was separated, dried over magnesium sulfate and concentrated in vacuo. Flash chromatography on 50 g of silica gel using 50:1:0.1 methylene chloride/methanol/ammonium hydroxide as the eluant afforded 1.12 g (90%) of the title compound as a foam.

Step C: 2-(R)-(1-(R)-(3,5-Bis(trifluoromethyl)phenyl) ethoxy)-3-(S)-(4-fluoro)phenyl-4-(3-(5-oxo-1,2,4-triazolo)methyl-morpholine A solution of 1.01 g (1.8 mmol) of 2-(R)-(1-(R)-(3,5-bis (trifluoromethyl)phenyl)ethoxy)-3-(S)-(4-fluoro)phenyl-4-(2-(N-methyl-carboxyacetamidrazono)morpholine in 15 mL of xylenes was heated at reflux for 2 hours. The reaction was cooled and concentrated in vacuo. Flash chromatography on 50 g of silica gel using 50:1:0.1 methylene chloride/methanol/ammonium hydroxide as the eluant afforded the title compound as a solid (79% yield). Mass Spectrum (FAB): m/Z 535 (M+H, 100%), 277 (60%). $^1$H NMR (CDCl$_3$+CD$_3$OD, 400 MHz, ppm): δ 1.48 (d, J=6.8, 3H), 2.52 (app t, J=10.4, 1H), 2.85–2.88 (m, 2H), 3.47 (d, J=2.8, 1H), 3.63 (d, J=14.4, 1H), 3.70 (dd, J=2.0, 11.6, 1H), 4.24 (app t, J=10.8, 1H), 4.35 (d, J=2.8, 1H), 4.91 (q, J=6.8, 1H), 7.07 (app t, J=8.4, 2H), 7.15 (s, 2H), 7.37–7.40 (m, 2H), 7.65 (s, 1H). Analysis: Calcd for C$_{23}$H$_{21}$F$_7$N$_4$O$_3$: C, 51.69; H, 3.96; N, 10.48; F, 24.88. Found: C, 51.74; H, 4.04; N, 10.50; F, 24.59.

EXAMPLE 8

Dimethyl titanocene

To a well stirred slurry of titanocene dichloride (CP$_2$TiCl$_2$) (249 g, 1.00 mol) in toluene (2.75 L) chilled to −5° C. (internal temp) was added methyl magnesium chloride (CH$_3$MgCl) (750 mL, 3.0M in THF, 2.25 mol) over 1 h, maintaining the temperature below 8° C. The resulting orange slurry is aged at 0–5° C. for 1 h, or until the insoluble purple CP$_2$TiCl$_2$ has dissolved. A NMR was taken to confirm reaction completion (see below), then the reaction was quenched into a solution of 6% aqueous ammonium chloride (700 mL), maintained at 0–5° C. The layers were separated and the organic phase was washed with cold water (3×575 mL) and brine (575 mL), then was dried with Na$_2$SO$_4$ (220 g). The filtered organic layer was evaporated to 1.5 Kg (maintaining an internal temperature of 25° or less). Weight % assay by $^1$H NMR showed the solution to contain 187 g product (90%, 12.5 wt % solution in toluene/THF). Typically, the material was greater than 95% pure, with only traces of the starting material and monomethyl intermediate. The solution may be further concentrated to 1.0 Kg, giving a 18 wt % solution in toluene, allowing for an easier assay. However, the presence of a small amount of THF increases the stability of the compound. The material was stored under nitrogen in a sealed carboy at 0° C. $^1$H NMR Cp$_2$Ti(CH$_3$)$_2$: δ 6.05 (s, 10H), −0.05 (s, 6H). CP$_2$TiCl(CH$_3$): δ 6.22 (s, 10H), 0.80 (s, 3H). Cp$_2$TiCl$_2$: δ 6.56 (s, 10H). $^{13}$C NMR Cp$_2$Ti(CH$_3$)$_2$: δ 113.20 (Cp$_2$), 45.77 ((CH$_3$)$_2$). Cp$_2$TiClCH$_3$: δ 115.86 (Cp$_2$), 50.37 (CH$_3$). Cp$_2$TiCl$_2$: δ 120.18.

EXAMPLE 9

4-Fluoro-α-[(phenylmethyl)amino]benzeneacetic acid

4-Fluorobenzaldehyde (7.0 kg, 56.4 moles) was added to a solution of sodium metabisulfite (5.76 kg, 30.3 moles) in water (50 L) and rinsed in with methanol (5 L). Sodium cyanide (2.83 kg, 57.7 moles) was added and rinsed in with water (3 L). The batch was stirred at 25° C. for 15 minutes before cooling to 8° C. A solution of benzylamine (6.04 kg, 56.4 moles) in methanol (11 L) was added. The batch was warmed to 34° C. and stirred for 2 hours. Water (23 L) was added and the batch was extracted with isopropyl acetate (30 L). The organic layer was washed with water (2×10 L) followed by saturated aqueous sodium chloride (10 L), then evaporated under reduced pressure to give a nitrile compound. The batch was dissolved in dimethylsulfoxide (50 L). Potassium carbonate (3.27 kg, 23.7 moles) was added and rinsed in with dimethylsulfoxide (6 L). Hydrogen peroxide solution in water (30%, 9.43 L, 83.2 moles) was added and the batch was stirred at room temperature overnight. The batch was diluted with water (120 L) and cooled to 13° C. The batch was filtered and the filter cake was washed with water (50 L). The resulting amide compound was dried on the filter, then slurried in industrial methylated spirits (38 L). A solution of sodium hydroxide pellets (3.27 kg, 81.75 moles) in water (11 L) was added to the batch and rinsed in with industrial methylated spirits (6 L).

After heating at reflux (80° C.) for 3.5 hours, the batch was distilled to low volume, removing the industrial methylated spirits. The batch was diluted with water (100 L) and extracted with isopropyl acetate (30 L). The layers were separated and the aqueous layer was acidified to pH 5–6 with concentrated hydrochloric acid. The precipitated solid was filtered and washed with water (2×10 L), then collected and dried under vacuum to give 12.3 kg (84% yield from 4-fluorobenzaldehyde) of 4-fluoro-α-[(phenylmethyl) amino]benzeneacetic acid.

EXAMPLE 10

4-Fluoro-α-[(phenylmethyl)amino]benzeneacetic acid methyl ester hydrochloride 4-Fluoro-α-[(phenylmethyl)amino]benzeneacetic acid (12.2 kg, 47.1 moles) was slurried in methanol (37 L), then hydrogen chloride gas was passed over the mixture. The resulting slurry was stirred at 35–45° C. for 3 hours, then concentrated to 30–35 L by distillation. Methyl-t-butyl ether (20 L) was added and the batch was seeded with 4-Fluoro-α-[(phenylmethyl)amino]benzeneacetic acid methyl ester hydrochloride. Upon development of the seed-bed, methyl-t-butyl ether (20 L) was added. The slurry was aged for 1 hour, then filtered. The filter cake was washed with methyl-t-butyl ether:methanol (95:5, 8.0 L), then dried under vacuum at 30° C. to give 12.2 kg (84% yield) of 4-fluoro-α-[(phenylmethyl)amino]-benzeneacetic acid methyl ester hydrochloride.

EXAMPLE 11

α-Amino-4-fluorobenzeneacetic acid methyl ester

4-Fluoro-α-[(phenylmethyl)amino]benzeneacetic acid methyl ester hydrochloride (12.2 kg, 39.4 moles) was added to a slurry of 10% palladium-on-carbon (1.2 kg) in isopropanol (50 L). Ammonium formate (5.0 kg, 79.4 moles) was added and the batch was heated to 50° C. Progress of the reaction was monitored by HPLC. The batch was filtered through Hyflo Supercel and the filter cake was washed with isopropanol (25 L). The filtrate was evaporated to low volume and flushed with isopropyl acetate (50 L). The residue was dissolved in isopropyl acetate (30 L) and washed with 5% aqueous potassium phosphate (40 L), followed by saturated aqueous sodium chloride (10 L). The solution was evaporated under vacuum to give 5.79 kg (87% yield) of racemic α-amino-4-fluorobenzeneacetic acid methyl ester. HPLC Conditions—Column: Zorbax Rx-C8, 25 cm×4.6 mm; Column temperature: 40° C.; Mobile phase: acetonitrile:0.1% aqueous phosphoric acid (70:30 v/v); Flow rate: 1 mL/min; Detection: UV at 220 nm; Approximate retention times: α-amino-4-fluorobenzeneacetic acid methyl ester: 2.2 minutes; 4-fluoro-α-[(phenylmethyl)amino] benzeneacetic acid methyl ester 2.6 minutes. If unreacted 4-fluoro-α-[(phenylmethyl)amino]-benzeneacetic acid methyl ester (>2%) remains after 1 hour, a second charge of 10% palladium-on-carbon (300 g) slurried in isopropanol (2.0 L) can be made, followed by ammonium formate (1.0 kg). Heating then continues until the reaction is complete.

EXAMPLE 12

(S)-α-Amino-4-fluorobenzeneacetic acid

A solution of racemic α-amino-4-fluorobenzeneacetic acid methyl ester (3.32 kg, 18.2 moles) in 96% ethanol (5 L) was filtered then water (500 mL) was added to it. A solution of di-O-benzoyl-D-tartaric acid (DBT, 1.32 kg, 3.7 moles) in water:ethanol (1:7, 2.86 L) was then added. The crystallization mixture was cooled to 5° C. and aged for 1.5 hours. The product was collected by filtration, washed with water:ethanol (1:7, 1.1 L), air dried, then dried under vacuum at 50° C. to give 1.91 kg of α-amino-4-fluorobenzeneacetic acid methyl ester, DBT salt (95.8% ee).

Solvent (6.6 L) was removed from the liquors by evaporation under reduced pressure. Benzaldehyde (120 mL) was added and the solution was stirred and heated at 50° C. for 4 hours. The solution was filtered and the solids were washed with water:ethanol (1:7, 2×150 mL) (chiral HPLC showed the filtrate to contain racemic α-amino-4-fluorobenzeneacetic acid methyl ester). A solution of di-O-benzoyl-D-tartaric acid (439 g, 1.23 moles) in water:ethanol (1:7, 960 mL) was added to the filtrate, which was then was cooled to 5° C. and aged for 1.5 hours. The product was collected by filtration, washed with water:ethanol (1:7, 2×1.1 L), air dried, then dried under vacuum at 50° C. to give 1.05 kg of α-amino-4-fluorobenzeneacetic acid methyl ester, DBT salt (95.4% ee). The combined yield of α-amino-4-fluorobenzeneacetic acid methyl ester, DBT salt was 2.96 kg (95% ee). The resolved (α-amino-4-fluorobenzeneacetic acid methyl ester, DBT salt was partitioned between methyl-t-butyl ether (5 L) and 5.5 M hydrochloric acid (6.2 L). The aqueous phase was washed with methyl-t-butyl ether (5 L), then filtered.

The α-amino-4-fluorobenzeneacetic acid methyl ester, DBT salt (2899 g, >95% ee) was partitioned between 5.5 M hydrochloric acid (6.2 L) and the second methyl-t-butyl ether extract from above. The aqueous phase was re-extracted with methyl-t-butyl ether (5 L) and filtered. The aqueous filtrates were combined and concentrated by slow distillation of solvent. The batch was cooled and aged at 5° C. for 2 hours. The product was collected by filtration and air dried for 30 minutes to give 4.055 kg of (S)-α-amino-4-fluorobenzeneacetic acid, hydrochloride salt (98.7% ee).
[1] Recrystallization from 5.5 M hydrochloric acid (5 L) gave (S)-α-amino-4-fluorobenzeneacetic acid, hydrochloride salt as a wet cake (3.28 kg, 99.8% ee). This wet cake was heated in a mixture of water (12 L) and concentrated hydrochloric acid (375 mL). Concentrated aqueous ammonia (1.2 L) and water (4 L) were added, then the batch was cooled to 20° C., and aged overnight. The product was collected by filtration, washed with water (6×4 L), air dried, then dried under vacuum at 50° C. for 24 hours to give 1.905 kg of (S)-α-amino-4-fluorobenzene-acetic acid free base (>99.7% ee, 48% yield from racemic α-amino-4-fluorobenzeneacetic acid methyl ester). Chiral HPLC Conditions: Column: Crownpak CR(+), 15 cm×4.5 mm; Column temperature: 40° C.; Mobile phase: pH 2.0 aqueous perchloric acid:methanol (95:5 v/v); Flow rate: 1 mL/min; Detection: UV at 220 nm; Approximate retention times: (R)-α-Amino-4-fluorobenzeneacetic acid: 2.9 minutes; (S)-α-Amino-4-fluoro-benzeneacetic acid: 5.6 minutes; (R) α-Amino-4-fluorobenzeneacetic acid methyl ester: 7.7 minutes; (S) α-Amino-4-fluorobenzeneacetic acid methyl ester: 14.0 minutes.

EXAMPLE 13

(S)-4-Fluoro-α-[(phenylmethyl)amino]benzeneacetate sodium salt

A solution of (S)-α-amino-4-fluorobenzeneacetic acid (1.00 kg, 5.91 moles) in aqueous sodium hydroxide (1 M, 5.91 L) was filtered and added to 10% palladium-on-carbon (25 g). A solution of benzaldehyde (941 g, 8.87 moles) was added and the batch was stirred under hydrogen (50 psi) for 4 hours. The batch was filtered and the filtrate was evaporated to residue under vacuum, then flushed with ethanol (2×3 L). The residue was slurried in boiling ethanol (1.5 L), then cooled to 15° C. The slurry was filtered and the filter cake was washed with cold ethanol (2×500 mL), then dried under vacuum at 55° C. to give 1.83 kg (92% yield) of (S)-4-fluoro-α-[(phenylmethyl)amino]-benzeneacetate sodium salt.

EXAMPLE 14

(S)-3-(4-Fluoropheny)-4-(phenylmethyl)-2-morpholinone hydrochloride (S)-4-Fluoro-α-[(phenylmethyl)-amino]benzeneacetate sodium salt (850 g, 3.02 moles) was added to 1,2- dibromoethane (4.85 kg, 25.8 moles) and diisopropylethylamine (419 g, 3.25 moles) in dimethylformamide (14.7 L). The batch was heated at 90° C. for 5 hours, then concentrated by distillation under vacuum to remove dimethylformamide. The residue was partitioned between ethyl acetate (3.2 L) and water (3.2 L). The aqueous layer was extracted with a second portion of ethyl acetate (2.0 L). The solution was dried over sodium sulfate, then filtered through a pad of silica (1.6 kg). The silica pad was rinsed with ethyl acetate (8.0 L) and the filtrate was evaporated under vacuum. The resulting residue was dissolved in a mixture of isopropanol (1.35 L) and ethyl acetate (400 mL), then filtered. A solution of hydrogen chloride gas in ethyl acetate (2.44 M, 1.34 L) was added and the slurry was aged in an ice bath for 1 hour. The slurry was filtered and the filter cake was washed with 1:1 isopropanol:ethyl acetate (600 mL), followed by methyl-t-butyl ether (600 mL). The solid was dried under vacuum to give 749 g (77% yield, 98% ee) of (S)-3-(4-fluoropheny)-4-(phenylmethyl)-2-morpholinone hydrochloride. Chiral HPLC Conditions: Column: Chiral (D)-Dinitrobenzoylphenyl-glycine (covalent) normal phase, 25 cm×4.6 mm; Column temperature: 35° C.; Mobile phase: hexane:ethanol (99:1 v/v); Flow rate: 1 mL/min; Detection: UV at 220 nm; Approximate retention times: (R)3-(4-Fluoropheny)-4-(phenylmethyl)-2-morpholinone: 16 minutes; (S)-3-(4-Fluoropheny)-4-(phenylmethyl)-2-morpholinone: 17 minutes.

EXAMPLE 15

Racemisation/Resolution of 3-(4-Fluorophenyl)-4-phenylmethyl-2-morpholinone

To a solution of 3-(4-fluorophenyl)-4-phenylmethyl-2-morpholinone (i.e. N-benzyl-4-fluorophenyl-1,4-oxazin-2-one) (10 g) in isopropyl acetate (110 ml) at room temperature was added a solution of (–)-3-bromocamphor-8-sulphonic acid ((–)-3BCS) (12 g) in acetonitrile (24 ml). Crystallisation began after 2–3 min. The slurry was stirred for 1 h at room temperature. Trifluoroacetic acid (7 ml) was added and the mixture stirred at 65° C. for 3 days. The mixture was cooled to 0–5° C., aged for 1 h. and the solid collected, washed with isopropyl acetate and dried in vacuo at 40° C., to give the N-benzyl-3-(S)-(4-fluorophenyl)-1,4-oxazin-2-one (–)-3BCS salt: yield 17.24 g, ee 98.6% (S) isomer. The chiral composition of the remaining liquors was determined as 79%(R), 21%(S). The liquors were stirred at 65° C. for 3 days, then cooled to 0–5° C. The solid was collected, washed with isopropyl acetate and dried in vacuo to give a further batch of the N-benzyl-3-(S)-(4-fluorophenyl)-1,4-oxazin-2-one (–)-3BCS salt: yield 0.84 g, ee 98.6% (S) isomer. The chiral composition of the remaining liquors was determined as 64%(R), 36%(S). The liquors were stripped in vacuo and the residue was dissolved in isopropyl acetate (20 ml) containing trifluoroacetic acid (1 ml) and stirred at 65° C. for 20 h. The mixture was cooled to 0–5° C. for 1 h and the solid collected, washed with isopropyl acetate and dried in vacuo to give a further batch of the N-benzyl-3-(S)-(4-fluorophenyl)-1,4-oxazin-2-one (–)-3BCS salt: yield 2.2 g, ee 99.2% (S) isomer. Total weight of (–)-3BCS salt: 20.28 g, 97% yield. A sample (0.5 g) of the (–)-3BCS salt was retained and the remainder converted back to free base. The salt was partitioned between isopropyl acetate (50 ml) and water (100 ml) containing 0.88 ammonia soln. (3 ml). The layers were separated and the aqueous phase extracted with isopropyl acetate (25 ml). The combined organic phases were washed with water (25 ml). The organic phase was concentrated to residue and flushed with isopropyl acetate to give the 3-(S)-(4-fluorophenyl)-4-phenylmethyl-2-morpholinone (i.e. N-benzyl-3-(S)-(4-fluorophenyl)-1,4-oxazin-2-one) as the free base: yield 8.7g, 93% recovery, ee 98.4% (S) isomer.

A further batch of N-benzyl-3-(S)-(4-fluorophenyl)-1,4-oxazin-2-one (–)-3BCS salt was prepared substantially according to the previous method except that the following quantities and reaction conditions were used: N-benzyl-3-(4-fluorophenyl)-1,4-oxazin-2-one (racemate) (4.96 g); (–)-3BCS in acetonitrile (1.85M; 9.4 ml); trifluoroacetic acid (2.1 ml); and isopropyl acetate (55 ml). The mixture was stirred at 90° C. for 6 days and then cooled to 0–5° C. and aged for 1 hour. The solid N-benzyl-3-(S)-(4-fluorophenyl)-1,4-oxazin-2-one (–)-3BCS salt was collected and washed with isopropyl acetate (20 ml). Yield 9.40 g (90%); ee 99.6% (S) isomer. The chiral composition of the remaining liquors was determined as 88% (R), 12% (S).

EXAMPLE 16

(2R-cis)-3,5-bis(Trifluoromethyl)benzeneacetic acid 3-(4-fluorophenyl)-4-(phenylmethyl)-2-morpholinyl ester A stirred suspension of (S)-3-(4-fluoropheny)-4-(phenylmethyl)-2-morpholinone hydrochloride (2.30 kg, 7.15 moles) in ethyl acetate (22 L) was treated with 10% aqueous sodium bicarbonate (22 L). The resulting organic solution was sequentially washed with 10% aqueous sodium bicarbonate (11 L) and water (2×11 L), then dried overnight with 4A molecular sieves (1 L). The solution was evaporated, then flushed with tetrahydrofuran (2×3 L) in order to remove traces of ethyl acetate. The resulting free base of (S)-3-(4-fluoropheny)-4-(phenylmethyl)-2-morpholinone was dissolved in tetrahydrofuran (19 L) and chilled to –75° C. L-Selectride (lithium tri-sec-butylborohydride, 6.74 L, 1.06 M, 7.15 moles) was added to the batch while maintaining the temperature at less than –70° C. The batch was aged for 15 minutes, then 3,5-bis(trifluoromethyl)benzoyl chloride (2.57 kg, 9.29 moles) was added, maintaining the temperature at less than –70° C. The reaction was monitored by HPLC. The reaction was quenched with acetic acid (205 mL) in tetrahydrofuran (800 mL), and the batch was allowed to warm to ambient temperature overnight. The solution was vacuum concentrated and the resulting oil was diluted with hexanes (36 L). The batch was washed sequentially with water (17 L), 10% aqueous sodium bicarbonate (3×8.5 L), and water (2×8.5 L), then dried overnight using 4A molecular sieves (1 L). The batch was assayed by HPLC to contain 2.44 kg (65% yield) of (2R-cis)-3,5-bis(trifluoromethyl)-benzeneacetic acid 3-(4-fluorophenyl)-4-(phenylmethyl)-2-morpholinyl ester. This batch was combined with another batch of (2R-cis)-3,5-bis(trifluoromethyl)benzeneacetic acid 3-(4-fluorophenyl)-4-(phenylmethyl)-2-morpholinyl ester (0.59 kg assay in 7 L hexanes) that was prepared just prior to the current batch. The combined batch solutions were filtered through a 20 μm line filter then diluted with hexanes (9 L). The crude (2R-cis)-3,5-bis(trifluoro-methyl)benzeneacetic acid 3-(4-fluorophenyl)-4-(phenyl-methyl)-2-morpholinyl ester solution (3.03 kg assay, 5.74 moles) was treated with hydrochloric acid in diethyl ether (9.6 L, 1.0 M), giving a white precipitate of (2R-cis)-3,5-bis(trifluoromethyl) benzeneacetic acid 3-(4-fluorophenyl)-4-(phenylmethyl)-2-morpholinyl ester hydrochloride salt (the hydrochloride salt was formed in order to remove tri-sec-butyl borane residue (from the L-Selectride)). The solid was collected by filtration, washed with hexanes (2×8 L), then dried under nitrogen. The hydrochloride salt of the product was broken by slurrying in a mixture of toluene (36 L) and 10% aqueous sodium bicarbonate (13 L). The resulting organic solution was washed with 10% aqueous sodium bicarbonate (13 L) and water (2×18 L). The toluene solution was assayed to contain 3.00 kg of (2R-cis)-3,5-bis(trifluoromethyl)-benzeneacetic acid 3-(4-fluorophenyl)-4-(phenylmethyl)-2-morpholinyl ester (80% by area, corrected for toluene). The batch was stored over 4A molecular sieves (1 L). HPLC conditions: Column: Zorbax RX-C8, 25 cm×4.6 mm; Mobile phase: acetonitrile:0.1% aqueous phosphoric acid (75:25, v/v); Flow rate: 1.5 mL/min; Detection: UV at 220 nm Approximate retention times: Reduced (S)-3-(4-fluoropheny)-4-(phenylmethyl)-2-morpholinone: 1.6 minutes; (S)-3-(4-fluoropheny)-4-(phenylmethyl)-2-morpholinone: 3.3 minutes; (2R-cis)-3,5-bis(trifluoromethyl)-benzeneacetic acid 3-(4-fluorophenyl)-4-(phenylmethyl)-2-morpholinyl ester: 9.2 minutes.

EXAMPLE 17

(2R-cis)-2-[[1-[3.5-bis(Trifluoromethyl)phenyl]ethenyl]oxy]-3-(4-fluorophenyl)-4-(phenylmethyl) mopholine A toluene solution of (2R-cis)-3,5-bis(trifluoromethyl)-benzeneacetic acid 3-(4-fluorophenyl)-4-(phenylmethyl)-2-morpholinyl ester (1.60 kg, 3.02 moles) was evaporated, then purged with nitrogen. Tetrahydrofuran (1.6 L) was added, followed by a solution of dimethyl titanocene in toluene (8.35 wt %, 1.73 kg of reagent, 8.31 moles) (prepared as noted below). The batch was sparged with nitrogen for 25 minutes, then heated to 80° C. The batch was aged in the dark for 5 hours at 80° C., then cooled to ambient temperature and aged overnight. The batch was solvent-switched to heptane by vacuum distillation, maintaining the temperature below 20° C. (126 L heptane added with concomitant distillation of 120 L) (the reaction mixture was solvent-switched to heptane and treated with bicarbonate buffered peroxide in order to precipitate the titanium residues). Water (22 L), sodium bicarbonate (2.0 kg), then 30% hydrogen peroxide (3.5 L) were added to the chilled (7° C.) mixture. The batch was stirred at ambient temperature overnight. The phases were partitioned, with much of the titanium residue remaining in the aqueous phase. The aqueous phase was back extracted with heptane (10 L), and the combined organic phases were filtered, washed with water (2–4 L), then concentrated. The crude product was recrystallized by dissolving in hot methanol (17 L), cooling to ambient temperature, then adding water (1.8 L). The material was isolated by filtration at 0° C. The filter cake was washed with 10% aqueous methanol (2 L, 0° C.), then the solid was dried at ambient temperature under nitrogen (1.45 kg of 94 wt % pure (2R-cis)-2-[[1-[3.5-bis(trifluoromethyl)-phenyl]-ethenyl]oxy]-3-(4-fluorophenyl)-4-(phenylmethyl) mopholine).

The dimethyl titanocene reagent may be prepared as follows. Methyl lithium (590 g, 26.9 moles) in a solution of diethyl ether (4.38% w/w, 13.5 kg) was added to a chilled (−8° C.), well-stirred slurry of titanocene dichloride (3.35 kg, 13.5 moles) in methyl-t-butyl ether (13.4 L) while maintaining the temperature below 5° C. The resulting slurry was aged at 0–5° C. for 1 hour. The reaction was quenched by adding water (8 L) while maintaining the temperature between 0 and 8° C. The organic phase was washed with cold water (4×3 L). The organic layer was then solvent-switched to toluene by distillation with concomitant addition of of toluene (24 L) while maintaining the temperature at 25° C. or less. Weight percent assay by $^1$H NMR showed the solution to contain 1.75 kg of dimethyl titanocene (63% yield, 8.35 wt % solution in toluene). The material was stored under nitrogen at 0° C. The progress of the reaction was followed by $^1$H NMR (250 MHz, CDCl$_3$, 10 second delay between pulses). Cp$_2$TiMe$_2$: $\partial$ (ppm) 6.05 (s, 10H), −0.05 (s, 6H); Cp$_2$TiClMe: $\partial$ 6.22 (s, 10H), 0.80 (s, 3H); Cp$_2$TiCl$_2$: $\partial$ 6.56 (s, 10H).

The dimethyl titanocene reagent alternatively may be prepared as follows. To a well stirred slurry of titanocene dichloride (CP$_2$TiCl$_2$) (6.0 g, 24.1 mmol) in toluene (72 mL) chilled to −5° C. was added dropwise methyl magnesium chloride (CH$_3$MgCl) (19.8 g, 19.2 mL, 3.0M in THF, 57.6 mmol, 2.4 eq) over 10 min, maintaining the temperature below 5° C. A viscous slurry was formed as magnesium chloride precipitated. The resulting slurry was aged at 0–5° for 50 min, during which time the insoluble red CP$_2$TiCl$_2$ had dissolved. A NMR assay on a quenched sample was taken to confirm reaction completion. A 0.2 mL sample was quenched into 1 mL of water and 1 ml of CDCl$_3$. The chloroform layer was used directly for NJR analysis. Dimethyl titanocene has resonances at 6.0 ppm (Cp) group and −0.2 ppm (CH$_3$ group). The monomethyl compound has resonances 0.2–0.3 ppm downfield, and the titanocene dichloride has resonance at 6.5 ppm. The reaction was then quenched by addition of a solution of 10% aqueous ammonium chloride (20 mL) over 10 min, maintaining the temperature below 10° C. The layers were separated and the organic phase was washed with cold water (3×20 mL) and brine (20 mL), then was dried with Na$_2$SO$_4$ (20 g). The filtered organic layer was concentrated under vacuum to approximately half volume. The total weight of the solution was 43 g, and NMR analysis showed 11.2 wt % in dimethyl titanocene (4.8 g, 96% yield). The THF level was 2%, however, the presence of a small amount of THF increases the stability of the reagent. The material was stored under nitrogen at 0° C.

Alternatively, the dimethyl titanocene reagent may be prepared as follows. To a well stirred slurry of titanocene dichloride (249 g, 1.00 mol) in toluene (2.75 L) chilled to −5° (internal temp) was added MeMgCl (750 mL, 3.0M in THF, 2.25 mol) over 1 h, maintaining the temperature below 8°. The resulting orange slurry is aged at 0–5° for 1 h, or until the insoluble purple CP$_2$TiCl$_2$ has dissolved. A NMR was taken to confirm reaction completion (see below), then the reaction was quenched into a solution of 6% aqueous ammonium chloride (700 mL), maintained at 0–5°. The organic phase was washed with cold water (3×575 mL) and brine (575 mL), then was dried with Na$_2$SO$_4$ (220 g). The filtered organic layer was evaporated to 1.5 Kg (maintaining an internal temperature of 25° or less). Weight % assay by $^1$H NMR showed the solution to contain 187 g product (90%, 12.5 wt % solution in toluene/THF). Typically, the material was greater than 95% pure, with only traces of the starting material and monomethyl intermediate. The solution may be further concentrated to 1.0 Kg, giving a 18 wt % solution in toluene, allowing for an easier assay. However, the presence of a small amount of THF increases the stability of the reagent. The material was stored under nitrogen in a sealed carboy at 0°. $^1$H NMR Cp$_2$TiMe$_2$: δ 6.05 (s, 10H), −0.05 (s, 6H). CP$_2$TiClMe: δ 6.22 (s, 10H), 0.80 (s, 3H). Cp$_2$TiCl$_2$: δ 6.56 (s, 10H). $^{13}$C NMR Cp$_2$TiMe$_2$: δ 113.20 (Cp$_2$), 45.77 (Me$_2$). Cp$_2$TiClMe: δ 115.86 (Cp$_2$), 50.37 (Me). Cp$_2$TiCl$_2$: δ 120.18.

HPLC conditions: Column: Zorbax RX-C8, 25 cm×4.6 mm; Mobile phase: acetonitrile:0.1% aqueous phosphoric acid (65:35, v/v); Flow rate: 1.5 mL/min; Detection: UV at

EXAMPLE 18

(2R-cis)-2-[[1-[3.5-bis(Trifluoromethyl)phenyl]ethenyl]oxy]-3-(4-fluorophenyl)-4-(phenylmethyl)mopholine A toluene solution of (2R-cis)-3,5-bis(trifluoromethyl)-benzeneacetic acid 3-(4-fluorophenyl)-4-(phenylmethyl)-2-morpholinyl ester [i.e. (4-benzyl-2-(R)-(3,5-bis(trifluoromethyl)benzoyloxy)-3-(S)-(4-fluorophenyl)-1,4-oxazine] solution contained 2.99 Kg, 5.67 mol) was evaporated into a 100 L flask. The flask was purged with nitrogen, then tetrahydrofuran (25 L) was added, followed by a solution of dimethyl titanocene in toluene/THF (12.5 wt %, 4.2 Kg contained reagent, 20.2 mol). The orange solution was sparged with nitrogen for 25 minutes, then was heated to 80° C. The reaction was aged in the dark for 4 h at 80° C., the was cooled to ambient temperature. Methanol (11.6L) and later (1.9 L) was added and the mixture was heated at 40° C. overnight, precipitating the titanium residues as a green solid. After cooling to ambient temperature, the solid was removed by filtration, the filtercake washed with toluene, and the resulting mother liquors were evaporated. The crude product was recrystallized by dissolving in hot methanol (30 L), cooling to ambient temperature, then adding water (3.4 L) over 3 h. The material was isolated via filtration at 0° C., the filtercake was washed with 0° C. 10% aq. methanol (2 L), and the solid was dried at ambient temperature under nitrogen, 2.55 Kg of (2R-cis)-2-[[1-[3.5-bis(Trifluoromethyl)phenyl]ethenyl]oxy]-3-(4-fluorophenyl)-4-(phenylmethyl)mopholine (85%) was isolated.

EXAMPLE 19

[2R-[2a(R*),3a]]-2-[1-[3,5-bis(Trifluoromethyl)phenyl]ethoxy]-3-(4-fluorophenyl)morpholine 4-methylbenzenesulfonate (salt)

A solution of (2R-cis)-2-[[1-[3.5-bis(trifluoromethyl)-phenyl]ethenyl]oxy]-3-(4-fluorophenyl)-4-(phenylmethyl)mopholine (1082 g, 94% pure, 1.94 moles) in 1:1 ethyl acetate:ethanol (13 L) was mixed with 10% palladium-on-carbon (165 g). The resulting slurry was treated with hydrogen (40 psi, 20–25° C.) for 12 hours. The reaction was monitored by hydrogen uptake and HPLC. The vessel was vented, and the catalyst was removed by filtration. After washing the catalyst with 1:1 ethyl acetate:ethanol (6 L) followed by ethyl acetate (2 L), the combined organic phases containing crude [2R-[2a(R*),3a]]-2-[1-[3,5-bis (Trifluoromethyl)phenyl]ethoxy]-3-(4-fluorophenyl)morpholine were vacuum concentrated. A second batch, starting with 1078 g of (2R-cis)-2-[[1-[3.5-bis(trifluoromethyl)phenyl]ethenyl]oxy]-3-(4-fluorophenyl)-4-(phenylmethyl)mopholine (1.93 moles) was prepared. The resulting crude [2R-[2a(R*),3a]]-2[1-[3,5-bis(trifluoromethyl)-phenyl]ethoxy]-3-(4-fluorophenyl)morpholine was vacuum concentrated and combined with the first batch. The combined batches of crude [2R-[2a(R*),3a]]-2-[1-[3,5-bis(trifluoromethyl)phenyl]ethoxy]-3-(4-fluorophenyl)morpholine were flushed with methyl-t-butyl ether (2×3 L) in order to remove residual ethyl acetate and ethanol, then were dissolved in methyl-t-butyl ether (3 L). The solution was assayed to contain 1348 g (3.09 moles, 80% yield) of [2R-[2a(R*),3a]]-2-[1-[3,5-bis(trifluoromethyl)phenyl]ethoxy]-3-(4-fluorophenyl)morpholine (as the free base). Alternatively, 60 g of the vinyl ether, 650 mL of methyl t-butyl ether (MTBE), and 18 g of 5% Pd on alumina were stirred under 40 psi hydrogen pressure at 40° for 12 H. Assay yield was 87%, with a 91:9 ratio of diastereomers. At the end of the reaction age, the catalyst was removed by filtration through SolkaFloc, then the filtrate was concentrated to 140 mL.

The first batch was treated with a warm (40° C.) solution of p-toluene sulfonic acid monohydrate (575 g, 3.03 moles) in methyl-t-butyl ether (3.2 L). The p-toluene sulfonic acid salt of [2R-[2a(R*),3a]]-2-[1-[3,5-bis(trifluoromethyl)phenyl]ethoxy]-3-(4-fluorophenyl)morpholine began to crystallize during the addition. The batch was cooled to ambient temperature and hexane (24 L) was added. The batch was aged for 2 hours, then the product was collected by filtration. The solid was washed with 4:1 hexane:methyl-t-butyl ether (2×2.5 L), then dried under nitrogen (1761 g (1655 g corrected for purity) of [2R-[2a(R*),3a]]-2-[1-[3,5-bis(trifluoromethyl)phenyl]-ethoxy]-3-(4-fluorophenyl)morpholine 4-methylbenzenesulfonate (salt), 94 wt % pure, 70% yield). Alternatively, to the second solution was added a solution of 16.0 g p-TsOH monohydrate in 64 mL MTBE at 35° over a 20 min period. The tosylate salt crystallized as a thick slurry. Then 520 mL of hexanes was added over 1 h, and the slurry was stirred 2 h at ambient temperature. The slurry was filtered, washed with 2×60 mL 1:4 MTBE:hexanes, and dried by air suction to give 51.9 g of the tosylate salt (75% yield) containing 0.9% of the undesired diastereomer. HPLC conditions: Column: Zorbax RX-C18, 25 cm×4.6 mm; Mobile phase: acetonitrile:aqueous 0.005 M sodium heptane sulfonate, 0.002 M potassium dihydrogen phosphate, 0.0005 M disodium hydrogen phosphate (75:25, v/v); Flow rate: 1.5 mL/min; Detection: UW at 220 nm; Approximate retention times: [2R-[2a(R*),3a]]-2-[1-[3,5-bis(trifluoromethyl)phenyl]-ethoxy]-3-(4-fluorophenyl)morpholine: 4.5 minutes; N-benzyl [2R-[2a(R*),3a]]-2-[1-[3,5-bis(trifluoromethyl)phenyl]-ethoxy]-3-(4-fluorophenyl)morpholine: 25.0 minutes; (2R-cis)-2-[[1-[3.5-bis(trifluoromethyl)-phenyl]-ethenyl]oxy]- 3-(4-fluorophenyl)-4-(phenylmethyl)mopholine: 30.0 minutes. HPLC conditions: Column: Zorbax RX-C18, 25 cm×4.6 mm; Mobile phase: acetonitrile:aqueous 0.005 M sodium heptane sulfonate, 0.002 M potassium dihydrogen phosphate, 0.0005 M disodium hydrogen phosphate (60:40, v/v); Flow rate: 1.5 mL/min; Detection: UV at 220 nm; Approximate retention times: [2R-[2a(R*),3a]]-2-[1-[3,5-bis(trifluoromethyl)phenyl]-ethoxy]-3-(4-fluorophenyl)morpholine: 9.0 minutes; Diastereomer of [2R-[2a(R*),3a]]-2-[1-[3,5-bis(trifluoro-methyl)phenyl]-ethoxy]-3-(4-fluorophenyl)morpholine: 11.0 minutes (epimeric at methyl group).

EXAMPLE 20

[2R-[2a(R*),3a]]-5-[[2-[1-[3,5-bis(trifluoromethyl)phenyl]ethoxy]-3-(4-fluorophenl)-4-morpholinyl]methyl]-1,2-dihydro-3H-1,2,4-triazol-3-one Powdered potassium carbonate (682 g, 4.93 moles) was added to a solution of [2R-[2a(R*),3a]]-2-[1-[3,5-bis(trifluoromethyl)-phenyl]-ethoxy]-3-(4-fluorophenyl)morpholine 4-methylbenzenesulfonate (salt) (1254 g, 2.06 moles), N-methylcarboxy-2-chloro-acetamidrazone (375 g, 2.26 moles), and dimethylformamide (10 L). The reaction was maintained between 15 and 25° C. and aged for 2.5 hours. The batch was diluted with 1:1 hexane:methyl-t-butyl ether (10 L) and 10.9% aqueous ammonium chloride (11 L). The phases were partitioned and the aqueous phase was back extracted with 1:1 hexane:methyl-t-butyl ether (2×8 L), followed by 1:2 hexane:methyl-t-butyl ether (8 L). The combined organic phases were washed with water (2×15 L), then vacuum concentrated. The resulting material was dissolved in xylenes (20 L) and heated to reflux (137° C.). The solution was maintained at reflux for 3 hours, then cooled to ambient temperature, whereupon [2R-[2a(R*),3a]]-5-[[2-[1-[3,5-bis(trifluoro-methyl)phenyl]ethoxy]-3-(4-fluorophenyl)-4-morpholinyl]methyl]-1,2-dihydro-3H-1,2,4-triazol-3-one crystallized. The batch was aged overnight, then filtered. The filter cake was washed with xylenes (2 L), then hexanes (2×2 L), then dried under vacuum at 30° C. for three days (696 g, 63% yield of [2R-[2a(R*),3a]]-5-[[2-[1-[3,5-bis(trifluoro-methyl)phenyl]ethoxy]-3-(4-fluorophenyl)- 4-morpholinyl]methyl]-1,2-dihydro-3H-1,2,4-triazol-3-one, i.e. 2-(R)-(1-(R)-(3,5-bis(trifluoro-methyl)-phenyl)ethoxy)-3-(S)-(4-fluoro)phenyl-4-(3-(5-oxo-1H,4H-1,2,4-triazolo)methylmorpholine).

Alternatively, the title product may be prepared as follows from the amine TsOH salt, (1.90 Kg, 3.12 mol); N-methylcarboxyl-2-chloroacetamidrazone (516.3 g, 3.12 mol); $K_2CO_3$ (1.08 kg, 2.5 eq.); and DMSO (15.6 L). To a suspension of amine salt and powder $K_2CO_3$ in DMSO (7.8 L) at 20° C. is added a solution of N-methylcarboxyl-2-chloroacetamidrazone in DMSO (7.8 L). The first half of the solution is added quickly, (with slight cooling with ice water bath) then the remaining half is added over a period of 1 hr. After the addition, the reaction is checked by LC, and the reaction is quenched with cold water (15 L) and methyl-t-butyl ether (MTBE) (30 L) solution. The organic layer is separated, and washed with water, sat. NaHCO3, brine, and water (20 L/each) respectively. The aqueous layers is back extracted with additional MTBE (15 L). The combined MTBE solution is concentrated to an oil. The resulting crude product is dissolved in xylene (25 L) and diisopropylethylamine (6.25 L) and is heated to reflux (~135° C.) and the reaction is monitored by LC. The reaction takes 4–6 hours to complete, the the reaction solution is cooled down to room temperature overnight and filter to get the title product (expect 1.33 kg, ~80%, typically purity 98.5A %). The resulting crude product is dissolved in hot methanol (13.3 L), added charcoal 133 g, then filtered and the charcoal is washed with hot methanol (3.3 L). The methanol solution is cooled down to room temperature, then water (7 L) is added dropwise. After being stirred at room temperature for 2 hrs, the suspension is filtered to isolate purified product (i.e. 2-(R)-(1-(R)-(3,5-bis(trifluoro-methyl)-phenyl)ethoxy)-3-(S)-(4-fluoro)phenyl-4-(3-(5-oxo-1H,4H-1,2,4-triazolo) methylmorpholine) as a white crystalline compound (expect 1.20 kg, 90% recovery, typical purity, 99.5A %). HPLC conditions: Column: Zorbax RX-C8, 25 cm×4.6 mm; Mobile phase: (A) acetonitrile, (B) 0.1% aqueous phosphoric acid; Linear gradient: 40:60 A:B to 70:30 A:B in 10 minutes; Flow rate: 1.5 mL/min; Detection: UV at 220 nm; Approximate retention times: Alkylated intermediate: 5.7 minutes; [2R-[2a(R*),3a]]-5-[[2-[1-[3,5-bis(trifluoro-methyl)phenyl]ethoxy]-3-(4-fluorophenyl)-4-morpholinyl] methyl]-1,2-dihydro- 3H-1,2,4-triazol-3-one: 8.2 minutes. A sample prepared by this process was subsequently identified as being polymorphic Form II. It was characterized by an X-ray powder diffraction pattern with key reflections at approximately: 12.6, 16.7, 17.1, 17.2, 18.0, 20.1, 20.6, 21.1, 22.8, 23.9, and 24.8° (2 theta).

EXAMPLE 21

Preparation of Form I of 2-(R)-(1-(R)-(3,5-bis (trifluoromethyl)-phenyl)ethoxy)-3-(S)-(4-fluoro) phenyl-4-(3-(5-oxo-1H,4H-1,2,4-triazolo) methylmorpholine Form I of 2-(R)-(1-(R)-(3,5-bis(trifluoromethyl)-phenyl) ethoxy)-3-(S)-(4-fluoro)phenyl-4-(3-(5-oxo-1H,4H-1,2,4-triazolo)methylmorpholine was prepared by swirling Form II of 2-(R)-(1-(R)-(3,5-bis(trifluoro-methyl)-phenyl) ethoxy)-3-(S)-(4-fluoro)phenyl-4-(3-(5-oxo-1H,4H-1,2,4-triazolo)methylmorpholine in isopropyl acetate at 25° C., followed by isolating the resultant solid by filtration.

Similarly, Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine was also prepared by swirling Form II of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo)methylmorpholine in ethanol, 2-propanol, water, methanol/water mixtures or acetonitrile at 25° C., followed by isolating the resultant solid by filtration.

EXAMPLE 22

Preparation of Seed Crystals of Form I of 2-(R)-(1-(R)-(3,5-bis(trifluoromethyl)-phenyl)ethoxy)-3-(S)-(4-fluoro)phenyl-4-(3-(5-oxo-1H,4H-1,2,4-triazolo) methylmorpholine A sample of Form II of 2-(R)-(1-(R)-(3,5-bis (trifluoromethyl)-phenyl)ethoxy)-3-(S)-(4-fluoro)phenyl-4-(3-(5-oxo-1H,4H-1,2,4-triazolo)methylmorpholine was placed in a small aluminum pan and the unsealed pan was placed in a Differential Scanning Calorimeteric Cell (DSC) instrument. The sample was heated from ambient temperature to 230° C., then cooled back down to room temperature. The resulting solid is suitable for use as seed crystals in the large-scale preparation of Form I of 2-(R)-(1-(R)-(3,5-bis (trifluoromethyl)-phenyl)ethoxy)-3-(S)-(4-fluoro)phenyl-4-(3-(5-oxo-1H,4H-1,2,4-triazolo)methylmorpholine

EXAMPLE 23

Preparation of Form I of 2-(R)-(1-(R)-(3,5-Bis (trifluoromethyl)-phenyl)ethoxy)-3-(S)-(4-fluoro) phenyl-4-(3-(5-oxo-1H,4H-1,2,4-triazolo) methylmorpholine A 22 liter flask was charged with Form II of 2-(R)-(1-(R)-(3,5-Bis(trifluoromethyl)-phenyl)ethoxy)-3-(S)-(4-fluoro)phenyl-4-(3-(5-oxo-1H,4H-1,2,4-triazolo) methylmorpholine (566 g) and 5.7 liters of methanol. The mixture was heated to reflux (65° C.) by which time all of the solids were in solution. The solution was allowed to cool to 50° C. and seeded with approximately 200 mg of Form I of 2-(R)-(1-(R)-(3,5-Bis(trifluoromethyl)-phenyl)ethoxy)-3-(S)-(4-fluoro)phenyl-4-(3-(5-oxo-1H,4H-1,2,4-triazolo) methylmorpholine and allowed to cool to 45° C. by which time a seedbed had formed. The mixture was cooled to 26° C. at which time 2.8 liters of water was added over a 1 hour period. The mixture was aged at room temperature for 2 hours, then heated to 70° C. for 2 hours to ensure complete conversion of all Form II material to Form I. The mixture was allowed to cool overnight, then it was chilled to 0° C., aged at 0° C. for 70 minutes, then filtered at −3° C. The collected material was dried on a filterpot with a nitrogen tent overnight and drypackaged to yield 549 g (97%).

EXAMPLE 24

Preparation of Form I of 2-(R)-(1-(R)-(3,5-Bis (trifluoromethyl)-phenyl)ethoxy)-3-(S)-(4-fluoro) phenyl-4-(3-(5-oxo-1H,4H-1,2,4-triazolo) methylmorpholine A pilot scale reaction vessel was charged with 2-(R)-(1-(R)-(3,5-Bis(trifluoromethyl)-phenyl)ethoxy)-3-(S)-(4-fluoro)phenyl-4-(3-(5-oxo-1H,4H- 1,2,4-triazolo) methylmorpholine (Form II) (14.5 kg) and 158 liters of methanol. The mixture was heated to 50° C. by which time all of the compound had dissolved. Activated charcoal (Darco G-60) (1.5 kg) was added via manhead as a slurry in 6 kg methanol and was flushed in with an additional 2 liters of methanol. The batch was heated to reflux (62° C.) and aged for 1 hour. The batch was then cooled to 60° C. and filtered through a 14" SS sparkler filter. After recycling for 10 minutes, no breaktrough was observed in the sightglass, so the recycle line was blown back to the reactor. The batch was then pumped through the sparkler, then through a 10μ and 0.6μ inline filter assembly, and finally to a receiving vessel. The line was blown forward, then 50 liters of methanol were added to the initial reaction vessel as a flush. The flush was recycled for 10 minutes, to clean the recycle line and to heat above ambient. Then it was transferred forward through the filters to the receiving vessel. The batch was then concentrated from ~210 liters to 170 liters via atmospheric distillation. A sample showed the desired concentration, 88 g/L (14.9 kgs, no losses). The batch was cooled to 50° C. and seeded with 300 grams of pure, Form I of 2-(R)-(1-(R)-(3,5-Bis(trifluoromethyl)-phenyl)ethoxy)-3-(S)-(4-fluoro)phenyl-4-(3-(5-oxo-1H,4H-1,2,4-triazolo) methylmorpholine. An extremely light seed bed formed, and crystals could barely be detected even at 45° C. The thin slurry was aged at 45° C. for an hour, yet showed little change in appearance. The thin slurry was allowed to cool to 25° C. overnight, resulting in a slurry with 60.5 g/L of dissolved compound. A sample of the wetcake idicated only Form I crystals. 83.6 kgs of water were then added (33 vol % to methanol) over 3 hours through the subsurface charge line. Samples indicated 0.1 wt % 030 in the supernatant, and all crystals were again Form I. The batch was cooled to 0° C. over 2 hours. The batch was then dropped to a large scale filter in a single drop. Approximately 15 kgs of 2:1 MeOH/Water cake wash were used to wash the vessel, yet there was still product holdup (possibly 500–1000 grams). The remaining 15 kgs of cake was were charged to the filter via a spray nozzle. 217.8 kgs of mother liquors and wash were collected (0.1wt % 030). The wetcake (14.8 kgs) was then dried overnight at 50° C. under 27.5" vacuum with a 0.2 SCFM sweep. After 12 hours, TG analysis showed 0.0% weight loss. Total batch package weight was 12.82 kgs of the title compound.

EXAMPLE 25

Typical Pharmaceutical Compositions Containing the Compound of the Invention

A: Dry Filled Capsules Containing 5 mg of Active Ingredient Per Capsule

| Ingredient | Amount per capsule (mg) |
| --- | --- |
| Active ingredient | 5 |
| Lactose | 194 |
| Magnesium stearate | 1 |
| Capsule (size No. 1) | 200 |

The active ingredient may be reduced to a No. 60 powder and the lactose and magnesium stearate may then be passed through a No. 60 blotting cloth onto the powder. The combined ingredients may then be mixed for about 10 minutes and filled into a No. 1 dry gelatin capsule.

B: Tablet

A typical tablet would contain the active ingredient (5 mg), pregelatinized starch USP (82 mg), microcrystalline cellulose (82 mg) and magnesium stearate (1 mg).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compound of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A polymorphic form of the compound 2-(R)-(1-(R)-(3,5-bis(trifluoromethyl)phenyl)ethoxy)-3-(S)-(4-fluoro) phenyl-4-(3-(5-oxo-1H,4H-1,2,4-triazolo) methylmorpholine characterized by an X-ray powder diffraction pattern with key reflections at approximately: 12.0, 15.3, 16.6, 17.0, 17.6, 19.4, 20.0, 21.9, 23.6, 23.8, and 24.8° (2 theta) which is substantially free of a polymorphic form of the compound 2-(R)-(1-(R)-(3,5-bis (trifluoromethyl)phenyl)ethoxy)-3-(S)-(4-fluoro)-phenyl-4-(3-(5-oxo-1H,4H-1,2,4-triazolo)methylmorpholine characterized by an X-ray powder diffraction pattern with key reflections at approximately: 12.6, 16.7, 17.1, 17.2, 18.0, 20.1, 20.6, 21.1, 22.8, 23.9, and 24.8° (2 theta).

2. A pharmaceutical composition comprising a pharmaceutically acceptable carrier and a polymorphic form of the compound 2-(R)-(1-(R)-(3,5-bis(trifluoro-methyl)phenyl) ethoxy)-3-(S)-(4-fluoro)phenyl-4-(3-(5-oxo-1H,4H-1,2,4-triazolo)methylmorpholine characterized by an X-ray powder diffraction pattern with key reflections at approximately: 12.0, 15.3, 16.6, 17.0, 17.6, 19.4, 20.0, 21.9, 23.6, 23.8, and 24.8° (2 theta) and which is substantially free of a polymorphic form of the compound 2-(R)-(1-(R)-(3,5-bis (trifluoromethyl)phenyl)-ethoxy)-3-(S)-(4-fluoro)phenyl-4-(3-(5-oxo-1H,4H-1,2,4-triazolo)-methylmorpholine characterized by an X-ray powder diffraction pattern with key reflections at approximately: 12.6, 16.7, 17.1, 17.2, 18.0, 20.1, 20.6, 21.1, 22.8, 23.9, and 24.8° (2 theta).

3. A method for antagonizing the effect of substance P at its receptor site or for the blockade of neurokinin-1 receptors in a mammal which comprises administering to the mammal the polymorphic form of claim 1 in an amount that is effective for antagonizing the effect of substance P at its receptor site or for the blockade of neurokinin-1 receptors in the mammal.

4. A method for the treatment or prevention of emesis in a mammal in need thereof which comprises administering to the mammal an effective amount of the polymorphic form of claim 1.

5. A method for the treatment or prevention of depression in a human in need thereof which comprises administering to the human an effective amount of the polymorphic form of claim 1.

6. A method for the treatment or prevention of anxiety in a human in need thereof which comprises administering to the human an effective amount of the polymorphic form of claim 1.

7. A method for the treatment or prevention of psychosis in a human in need thereof which comprises administering to the human an effective amount of the polymorphic form of claim 1.

8. A method for the treatment or prevention of schizophrenia in a human in need thereof which comprises administering to the human an effective amount of the polymorphic form of claim 1.

* * * * *